United States Patent
Brobst et al.

(10) Patent No.: US 11,791,038 B1
(45) Date of Patent: Oct. 17, 2023

(54) MACHINE LEARNING SYSTEM FOR ASYMMETRICAL MATCHING OF CARE GIVERS AND CARE RECEIVERS

(71) Applicant: IntelliCentrics, Inc., Flower Mound, TX (US)

(72) Inventors: Stephen Brobst, Las Vegas, NV (US); Michael Sheehan, Flower Mound, TX (US); John Trustman, Frisco, TX (US); Michael McDonald, Dallas, TX (US)

(73) Assignee: Zengine Limited, London (GB)

( * ) Notice: Subject to any disclaimer, the term of this patent is extended or adjusted under 35 U.S.C. 154(b) by 0 days.

(21) Appl. No.: 17/979,602

(22) Filed: Nov. 2, 2022

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC ............................. G16H 40/20; G16H 10/60
See application file for complete search history.

(56) References Cited

U.S. PATENT DOCUMENTS

| | | | |
|---|---|---|---|
| 9,424,532 B1 | 8/2016 | Abedini et al. | |
| 9,860,391 B1 | 1/2018 | Wu et al. | |
| 10,127,234 B1 * | 11/2018 | Krishnan et al. | |
| 10,718,031 B1 | 7/2020 | Wu et al. | |
| 10,997,703 B1 | 5/2021 | Khalatian | |
| 11,238,469 B1 | 2/2022 | Talvola et al. | |
| 11,282,153 B1 | 3/2022 | Albro et al. | |
| 11,294,979 B2 | 4/2022 | Makani et al. | |
| 2005/0075904 A1 * | 5/2005 | Wager et al. | |
| 2009/0198509 A1 | 8/2009 | Dumoff | |
| 2012/0010932 A1 | 1/2012 | Satyavolu et al. | |

(Continued)

FOREIGN PATENT DOCUMENTS

WO 2022246458 A1 11/2022

*Primary Examiner* — Michael Tomaszewski
*Assistant Examiner* — William T. Monticello

(57) ABSTRACT

A system for selection of a medical provider (MP) by a requesting patient based on preferences for the MP includes a first model modeling the preferences of a plurality of patients for select MPs and trained on a first training data set comprised of patients and MPs. The patients in the first training data set have rated at least one of the MPs in the first data set by a predetermined set of patient determined preferences. A second model is provided for modeling the preferences of a plurality of MPs for select patients and trained on a second training data set comprised of MPs and patients. The MPs in the second training data set have rated at least one of the patients in the second data set by a predetermined set of MP determined preferences. An available MP data set is provided containing information representative of available MPs for selection thereof by the requesting patient. A controller controls the first and second models to select at least a portion of the available MPs in the available MP data set for input of the associated representative information to the first and second model MP inputs. A list generator generates a ranked list of available MPs from the output of the first model for the requesting patient. A combiner modifies the ranked list of available MPs by the output of the second model to output a modified ranked list.

20 Claims, 21 Drawing Sheets

(56) References Cited

U.S. PATENT DOCUMENTS

| | | | |
|---|---|---|---|
| 2013/0173284 A1 | 7/2013 | Hyde et al. |
| 2014/0046675 A1 | 2/2014 | Harwood et al. |
| 2015/0019247 A1 | 1/2015 | Stedillie |
| 2015/0088541 A1 | 3/2015 | Yao |
| 2015/0213202 A1* | 7/2015 | Amarasingham et al. |
| 2018/0025407 A1* | 9/2018 | Zhang et al. |
| 2018/0285986 A1 | 10/2018 | Perry et al. |
| 2019/0318317 A1 | 10/2019 | Sergott et al. |
| 2021/0182113 A1* | 6/2021 | Freese et al. |
| 2021/0265063 A1* | 8/2021 | Karampourniotis et al. |
| 2022/0067665 A1* | 3/2022 | Westerheide et al. |
| 2022/0336088 A1* | 6/2022 | Thomas et al. |
| 2022/0215928 A1* | 7/2022 | Tabak et al. |
| 2022/0261927 A1 | 8/2022 | Emile et al. |
| 2022/0284324 A1 | 9/2022 | Khalatian |
| 2022/0318930 A1 | 10/2022 | Prisby et al. |

\* cited by examiner

| MP | Ø1 | Ø2 | Ø3 | Ø4 | Ø5 | Ø6 | Ø7 |
|---|---|---|---|---|---|---|---|
| PRACTICE AREA | | | | | | | |
| • SPECIALTY | | | | | | | |
| • SUB-SPECIALTY | | | | | | | |
| GENDER | | | | | | | |
| AGE | | | | | | | |
| ETHNICITY | | | | | | | |
| LOCATION | | | | | | | |
| EXPERIENCE (YEARS) | | | | | | | |
| INSURANCE (GROUP) | | | | | | | |
| RELIGIOUS AFFILIATION | | | | | | | |

MP-MP DATABASE ($\bar{x}_{MP\text{-}mp}$)

FIG. 12

MP-PATIENT DATABASE ($\vec{x}_{MP\text{-}p}$)

| PATIENT | A | B | C | D | E | F | G | H |
|---|---|---|---|---|---|---|---|---|
| AGE | | | | | | | | |
| GENDER | | | | | | | | |
| ETHNICITY | | | | | | | | |
| MALADY | | | | | | | | |
| WEIGHT | | | | | | | | |
| LOCATION | | | | | | | | |
| INCOME BRACKET | | | | | | | | |
| RELIGIOUS AFFILIATION | | | | | | | | |

FIG. 13

| PATIENT/MP | A | B | C | D | E | F | G |
|---|---|---|---|---|---|---|---|
| PREFERENCE | | | | | | | |
| • TEMPERAMENT | | | | | | | |
| • COMPLIANCE | | | | | | | |
| • HONESTY | | | | | | | |
| • APPEARANCE | | | | | | | |
| • TALKATIVE | | | | | | | |
| • INTELLIGENCE | | | | | | | |
| • KNOWLEDGE | | | | | | | |
| • RELIGIOUS AFFILIATION | | | | | | | |

$\vec{y}_{MP}$

FIG. 14

PATIENT-MP DATABASE ($\vec{x}_{P\text{-}mp}$)

| MP | Ø1 | Ø2 | Ø3 | Ø4 | Ø5 | Ø6 | Ø7 | Ø8 |
|---|---|---|---|---|---|---|---|---|
| PRACTICE AREA SPECIALTY | | | | | | | | |
| SUB-SPECIALTY | | | | | | | | |
| GENDER | | | | | | | | |
| AGE | | | | | | | | |
| ETHNICITY | | | | | | | | |
| LEGAL ACTIONS | | | | | | | | |
| INSURANCE | | | | | | | | |
| PAYMENT TERMS | | | | | | | | |
| RELIGIOUS AFFILIATION | | | | | | | | |
| LOCATION | | | | | | | | |
| OFFICE HOURS | | | | | | | | |
| ONLINE RATINGS | | | | | | | | |

FIG. 16

PATIENT-PATIENT DATABASE ($\vec{x}_{P\text{-}p}$)

| PATIENT | A | B | C | D | E | F | G | H |
|---|---|---|---|---|---|---|---|---|
| AGE | | | | | | | | |
| GENDER | | | | | | | | |
| MEDICAL PROFILE | | | | | | | | |
| WEIGHT | | | | | | | | |
| LOCATION | | | | | | | | |
| INCOME BRACKET | | | | | | | | |
| RELIGIOUS AFFILIATION | | | | | | | | |
| ACTIVITIES | | | | | | | | |

FIG. 17

| MP/PATIENT | $\vec{y}_p$ | | | | | |
|---|---|---|---|---|---|---|
| | ∅1 | ∅2 | ∅3 | ∅4 | ∅5 | ∅6 |
| PREFERENCE | | | | | | |
| • BEDSIDE MANNER | | | | | | |
| • INFORMATIVE | | | | | | |
| • TIMELY | | | | | | |
| • THOROUGH | | | | | | |
| • GENDER | | | | | | |
| • PERSONALITY | | | | | | |
| • FOLLOW UP | | | | | | |
| • COMMUNICATION | | | | | | |

FIG. 18

PATIENT A'

| MP | A' | Ø1 | Ø2 | Ø3 | Ø4 | Ø5 | Ø6 | Ø7 | Ø8 | Ø9 | Σ | ÷2 |
|---|---|---|---|---|---|---|---|---|---|---|---|---|
| Ø1 | 3 | 2 | | | | | | | | | 5 | 2.5 |
| Ø2 | 1 | | 7 | | | | | | | | 8 | 4 |
| Ø3 | 7 | | | 4 | | | | | | | 11 | 5.5 |
| Ø4 | 8 | | | | 1 | | | | | | 9 | 4.5 |
| Ø5 | 7 | | | | | 8 | | | | | 15 | 7.5 |
| Ø6 | 4 | | | | | | 3 | | | | 7 | 3.5 |
| Ø7 | 2 | | | | | | | 9 | | | 11 | 5.5 |
| Ø8 | 10 | | | | | | | | 2 | | 12 | 6 |
| Ø9 | 5 | | | | | | | | | 3 | 8 | 4 |

MACHINE LEARNING SYSTEM FOR ASYMMETRICAL MATCHING OF CARE GIVERS AND CARE RECEIVERS

TECHNICAL FIELD

The present invention relates to the prioritization of medical provider rank lists for a patient, and more particularly, for generating a medical provider rank list based on preferences of both patients and medical providers and monitoring the results of previous rank lists.

BACKGROUND

In certain industries that provide service, there is a desire to deliver the services in accordance with a particular customer's preferences. One such system is the medical industry. In the medical industry, a new patient has a desire to select a medical provider in any particular medical system in accordance with their personal preferences. Thus, a new patient can be provided access to all of the available medical practitioners to make a selection. This can be difficult for the new patient, as they have to wade through a lot of information in order to select a particular medical provider that suits their needs. Medical providers provide information to the system in the form of profile information to allow the patient to make an informed selection. Filters and the such can be employed to trim down the amount of information that is presented to the new patient.

Even though a new patient may be provided with a select amount of filtered information regarding potential medical providers that might meet the needs of that new patient, there is also an issue with respect to preferences of the medical provider. It is very disconcerting to make a selection of a preferred medical provider just to find out that the medical provider does not want to accept the new patient. This situation can arise for a number of different reasons. For example, a new patient may select a medical provider based upon their education, experience, online ratings, gender, etc. An additional parameter for selection of a medical provider by a patient might be that the medical provider is a female, and this is an important decision-making point. On the medical provider's side of the decision as to preferences, the medical provider does not really factor in their gender relative to accepting a new patient. A consideration of the medical provider in order to accept the new patient, for example, might be that the new patient be younger than 40. This is a preference by the medical provider but has no bearing on the decision on the new patient's side of the decision. Therefore, a medical provider, if ranking patients, would generally rank patients over the age of 40 relatively low. This is not something that a new patient with access would really be concerned with. This could also be the case with respect to a patient with a certain malady that might fit within the expertise of a particular medical provider, but that medical provider has a negative preference for taking patients with that particular malady. Even though the patient might rank this particular medical provider relatively high on their decision-making side, the fact that the medical provider ranks this particular new patient low in their decision-making side is not typically factored into the overall decision-making process.

In the decision-making process employed by a patient seeking out a medical provider, there are a number of different approaches that a patient might take. A first approach might be to just do a search of a database of available medical providers and then just scan through their credentials. The patient has to rely upon their experience with respect to any particular malady they might have and how much they have interfaced with the medical system and the associated medical providers needed to address this particular malady. If, which is typically the case, this particular patient has never been faced with this particular malady and has no idea how to intelligently select a medical provider from the provided list. If the malady was, for example, a broken hip from a traumatic injury, the patient would have to make a fairly quick decision and looking up orthopedic surgeons from just a general list of surgeons is difficult for patient never having been faced with this particular situation before. The patient may realize this and seek advice from others. One approach is to seek advice from an emergency room physician, for example, and just take their recommendation. This is fairly typical. This approach, however, has very little reasoning behind the decision other than—the orthopedic surgeon was recommended by a physician, and this must be good. Another approach is to try and make a more informed decision by asking friends who have been faced with a similar malady and asking their opinions. They might just ask multiple friends who they recommend as an orthopedic surgeon and then make a decision based upon each friend's input as to that particular friend's preference for any particular orthopedic surgeon. This might present to the patient multiple orthopedic surgeons to select from. However, none of the above decision approaches factor in the preferences of the orthopedic surgeons.

SUMMARY

The present invention, as disclosed and described herein, comprise a system for selection of a medical provider (MP) by a requesting patient based on preferences for the MP. A first model is provided for modeling the preferences of a plurality of patients for select MPs and trained on a first training data set comprised of patients and MPs. The patients in the first training data set have rated at least one of the MPs in the first data set by a predetermined set of patient determined preferences. The first model has a first model patient input for receiving information representative of the requesting patient, a first model MP input for receiving information representative of an available MP and a MP preference output for outputting a patient determined preference of the requesting patient for an available MP based on a learned representation of the patient determined preferences in the first training data set. A second model is provided for modeling the preferences of a plurality of MPs for select patients and trained on a second training data set comprised of MPs and patients. The MPs in the second training data set have rated at least one of the patients in the second data set by a predetermined set of MP determined preferences, the second model having a second model patient input for receiving information representative of the requesting patient, a second model MP input for receiving information representative of an available MP and an MP determined preference output for outputting an MP determined preference of an available MP for the requesting patient based on a learned representation of the MP determined preferences in the second training data set. An available MP data set is provided containing information representative of available MPs for selection thereof by the requesting patient. A controller controls the first and second models to select at least a portion of the available MPs in the available MP data set for input of the associated representative information to the first and second model MP inputs. A list generator generates a ranked list of available MPs from the preference output of the first model for the requesting patient. A combiner modifies the ranked list of available MPs by the preference output of the second model to output a modified ranked list.

BRIEF DESCRIPTION OF THE DRAWINGS

For a more complete understanding, reference is now made to the following description taken in conjunction with the accompanying Drawings in which:

FIG. 12 illustrates a tabular view of the medical provider data set for the medical provider vector for training of the medical provider model;

FIG. 13 illustrates a tabular view of the patient data set for the patient vector for training of the medical provider model;

FIG. 14 illustrates a tabular view of the medical provider preference data set for the medical provider preference output vector for training of the medical provider model;

FIG. 16 illustrates a tabular view of the medical provider data set for the medical provider vector for training of the patient model;

FIG. 17 illustrates a tabular view of the patient data set for the patient vector for training of the patient model;

FIG. 18 illustrates a tabular view of the preference data set for the patient preference output vector for training of the patient model;

FIG. 21 illustrates a tabular view of the reconciliation between medical provider predicted preferences and patient predicted preferences;

DETAILED DESCRIPTION

Figure 1:
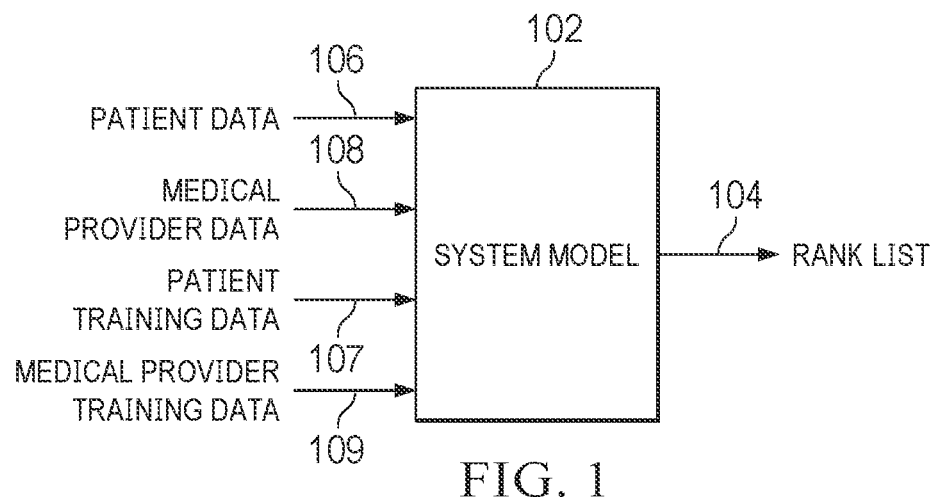
FIG. 1 illustrates a manner for combing patient and medical provider data within a system model.

Referring now to the drawings, wherein like reference numbers are used herein to designate like elements throughout, the various views and embodiments of a machine learning system for asymmetrical matching of care givers and care receivers are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to the drawings, and more particularly to FIG. 1, there is illustrated the manner in which patient and medical provider data may be combined within a system model to generate rank lists for the medical providers. A system model 102 which, in one embodiment, comprises a mathematical model which provides a model based upon training data relating to patient choices/preferences and medical provider choices/preferences, is used for generating a rank list output 104 of medical providers. (As used herein, the term "preferences" can be just a single yes or no choice, or it can be a graded value, wherein this could just be a ranking on the basis of 0-10). The system model 102 generates the rank list output 104 based on both patient data 106 and medical provider data 108. This patient data 106 is data that relates to a particular patient requesting information on medical providers. The patient data is in the form of information about that particular patient which the system model 102 is designed to receive as an input. There can be, of course, a voluminous amount of information possessed by a record system containing information regarding that patient or just information provided by the patient or combination of both. All or a certain subset of that information can be provided as an input to the system model 102. The medical provider data 108, by comparison, is information regarding a plurality of medical providers. Each medical provider contained in the medical provider data 108, as was the case with the patient, is associated with certain information that can be received by the system model 102. In the operation of the system model 102, as will be described in more detail herein below, the system model 102 sequences through each of the medical provider's information for processing thereof. After the information for all of the medical providers is sequence through, the rank list 104 is generated.

The system model 102 is initially trained using a statistically significant amount of training data including patient training data 107 and medical provider training data 109 from a large number of patients and medical providers. As will be described in more detail herein below, the training operation involves training from the perspective of the patient and their preferences with respect to medical providers. This will result in a portion of the model 102 having a trained representation of patient preferences for medical providers. As such, a new patient can be represented by sufficient input information to the system model 102 that, when input to the system model, will allow this trained representation of patient preferences for medical providers to determine what other patients that are substantially similar to the new patient will think regarding any of the available medical providers in the medical provider data 108. This training information enables the system model 102 to be created that comprises a representation of the patient preferences for a medical provider based upon the data set that comprises the patient training data 107 and medical provider preferences for a patient based upon the data set that comprises the medical provider training data 109. This basically yields two representations, each comprised of weighted parameters therein that provide a trained or learned representation of the patient choices/preferences for medical providers and and medical provider choices preferences for patients.

The patient data 106, during operation of the system model 102, illustrates an input from one or more patients that enables the input medical provider data 108 to operate within the system model 102 for the generation of the rank list 104. The representation embodied in the system model 102 may be implemented using a variety of learning mechanisms as will be more fully described herein below. The output rank list 104 provides a list of medical providers to a requesting patient making an inquiry that are most likely to be desired by the requesting patient providing the patient data 106 as inputs to the system model 102. As noted hereinabove and as will be more fully described hereinbelow, the patient data 106 relates directly to the requesting patient, whereas the information in the patient training data 106 and the medical provider training data 109 may not actually contain any information regarding this particular requesting patient, as the requesting patient may never have input prior data that can be used in the training or learning operation. A patient as defined within the confines of the system model 102 is just a representation embodied within input parameters or values that define the patient input to the system model 102. This could be things such as the particular malady being inquired about, personal information about a patient, medical history of the patient, etc. Additionally, the same is true about the medical provider data 108, as this just provides information about each of a plurality of medical providers contained within a data set of available medical providers. Each of the medical providers is defined by a representation embodied within input parameters or values that define the medical provider input to the system model 102. Again, as was the case with the patient data, any particular medical provider that provides information within the medical provider data 108 may or may not be included within the data set associated with the medical provider training data 109, as will be described in more detail in below.

The rank list output 104 is based upon a combination of the result of processing the provided patient data 106 and the available medical provider data 108 through the system model 102 such that the rank list 104 selections are based first upon the preferences of all of the patients that are similar to the requesting patient for medical providers, as embodied in the patient training data 107. The portion of the system model 102 associated with the patient preferences for a medical provider is utilized to determine how patients in the patient training data 107 that are similar to the requesting patient would have "ranked" a particular medical provider in the patient training data 107 based upon the preferences of that patient in the patient training data 107 for a medical provider in the patient training data 107 that is similar to any one of the medical providers in the medical provider data 108. As such, the system model 102, during operation, receives the patient data and then sequences through each available medical provider in the medical provider data 108 to determine a preference or ranking. The portion of the system model 102 associated with the medical provider preferences for a patient, on the other hand, is utilized to determine how each of the medical providers in the medical provider training data 109 that are similar to each processed one of the medical providers in the medical provider data 108 would have "ranked" a particular patient in the medical provider training data 109 based upon the preferences of that medical provider in the medical provider training data 109 for a patient in the medical provider training data 109 that is similar to the requesting patient in the patient data 108.

As will be described in more detail hereinbelow, the resulting rank list 104 output is a combination of what a generic medical provider prefers in a patient and what a generic patient prefers in a medical provider. For example, it may be that the trained representation of a generic male physician in a sports medicine practice results in a high ranking for a patient to be primarily male between the ages of 18 to 25 and to primarily play softball (it could be that softball is the major sport in a particular locale). Thus, the data to train this portion of the model would rank patients accordingly from the perspective of a male medical provider in a sports medicine practice. A 20-year-old female softball player patient would be ranked lower in this model than a 20-year-old male softball player patient. But that ranking would change if the male softball player patient was 25 years old by decreasing his ranking. If he played a different sport, that would also decrease his ranking. That is on the medical provider's side of the model training as to ranking wherein the ranking is provider based, i.e., it is what the generic male medical provider in the sports medicine practice desires. If a male physician in a sports medicine practice used the model to select a patient, which is not the case, the model would rank each patient based upon the training data upon which the model was trained. This side of the model is trained on the desires of a large number of sports medicine physicians with different desires and how they each rank different patients. This example just highlights the preferred patient based on many inputs, again from the medical provider's perspective.

On the patient's side of the model training, consider the example of a model that provides a trained representation of the physician's desire of a generic patient having a preferred treatment pattern, wherein the physicians are ranked. Suppose by way of example that the model results in a trained representation for a generic patient wherein (based upon the training) the generic patient primarily desires a physician in a natural medicine practice that specializes in treatment of illnesses using natural medicines rather than pharmaceutical based medicines. The model would thus rank a physician in a practice that specialized in natural medical treatments highly. But, if the physician utilized pharmaceutical based treatments, they would rank lower. But suppose that a first physician was a physician in a practice that specialized in medical treatments using plant based pharmaceutical medicines. And a second physician was a physician in a practice that specialized in treatments using new pharmaceutical medicines. Each of these would be ranked lower than the ideal selection. Thus, for the patient's side of the model, a natural medicine preferring patient, when selecting a physician, the model would rank the physicians accordingly based upon the training.

The result of both the provider's side of the model and the associated training and the patient's side of the model based on the associated training results in two rankings. The medical provider does not make any decisions based upon the patient's medical treatment preferences and the ranking on the provider's side of the model does not take that into account in the ranking, i.e., it is not trained on that input. Similarly, the model on the patient's side does not take into account age in the ranking, i.e., it is not trained on that input. The overall model would then have to merge these two rankings into a combined ranking. Suppose that the patient was 20 years old that desires pharmaceutical medicine treatment, resulting in a ranking of maybe three out of ten on the physician's side of the model because the patient did not desire natural based medicines. Suppose a physician that specialized in pharmaceutical based medical treatment, resulting in a ranking of nine on the patient's side of the model. Now, this physician ranks high on the patient's side, bur not high on the physician's side. The overall system model 102 would place this physician at maybe six on the rank list 104, because, although not ideal from the physician's perspective, it is highly ranked by the patient. Here, the patient is looking for a provider and the system model would not rank the provider at a nine because the patient is not a good fit for the physician from the physician's perspective. There are many factors upon which the model can be trained and all of these can be provided as a set of inputs for the input vector for the model. This will be described in more detail hereinbelow.

Figure 2:
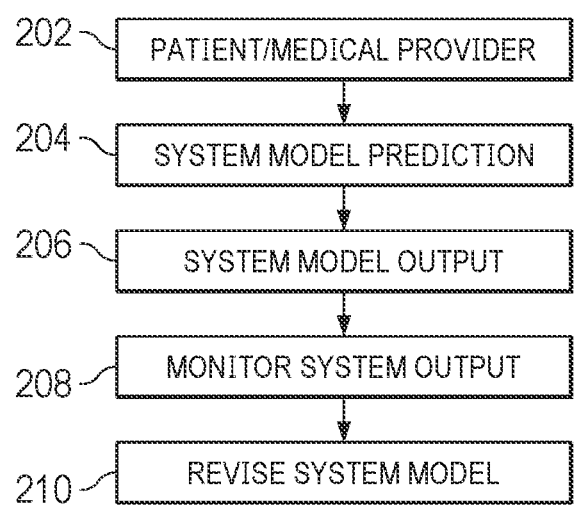
FIG. 2 illustrates a flow diagram of the operation of the overall system model.

Referring now to FIG. 2, there is illustrated a flow diagram of the general operation of the overall system model of FIG. 1. The patient training data 107 and medical provider training data 109 are provided at step 202. The patient training data 107 and medical provider training data 109 may be provided from any number of patients and medical providers, noting that the patient training data 107 and the medical provider training data 109 will typically be two different data sets. Each of the data sets will contain both medical provider and patient data in addition to preference data of, for the patient training data 107, patient preferences/rankings for physicians and, in the medical provider training data 109, medical provider preferences/rankings for patients. However, the accuracy of the system model 102 prediction that is generated in step 204 will more accurately provide medical provider rankings from new input patient data for requesting patient when a statistically significant training data set of patient training data 107 and medical provider training data 109 are used for establishing the initial system model generation. Using all of this data provided from a plurality of patients and medical providers, a system model prediction is created at step 204. The system model prediction comprises a stored representation having various weighted parameters that have been constructed from the patient/medical provider data from step 202. The system model provides a system model output at 206 responsive to provided patient input data from a requesting patient. The selections made for the ranked medical providers within the system model output are based on the stored representation within the system model that has been established based upon the training data provided at step 204. The system model output is monitored at step 208 to provide further improvements to the system model based upon the outputs that are being monitored. Based upon the monitored output and further information providing for example information on patient satisfaction or medical provider input, the system model may be further revised at step 210 to provide a better ranking of medical providers in future outputs based upon a singular user input.

Figure 3:
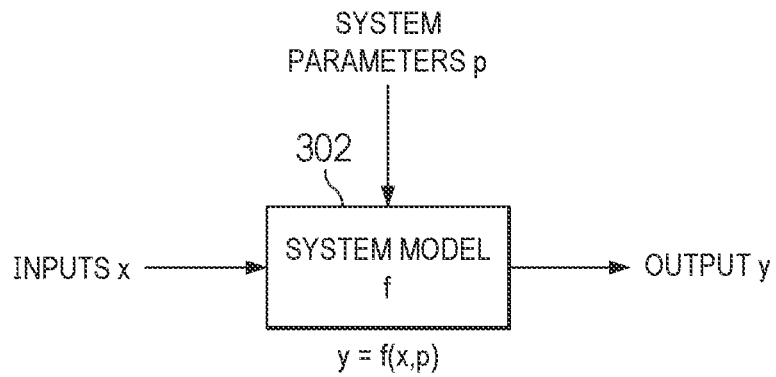
FIG. 3 illustrates a functional representation of a system model.

Referring now to FIG. 3, there is provided a generic representation of an overall system model 302. The system model 302 provides a stored representation of the system, i.e., the combined desires of the medical providers and the patients, that is trained on the patient training data 107 and medical provider training data 109 that have been provided in order to establish the model.

Modeling is used to define the operation of systems. In the current system, the choices of a combination of patient preferences and doctor preferences are modeled. A system is defined as a collection of choices that make up a process of interest. To facilitate the modeling and assessment of the system, a representation of the model is constructed. A model represents the choices of a combination of doctors and patients as a set of computational or logical associations. Models can be static, representing a system in a particular point in time, or dynamic, representing how the system changes with time. The model can also be a learning model that continuously updates (adapts) based upon the receipt of additional system inputs wherein the model is continuously updated as more and more data inputs are received. A set of variables that describe the system at any particular point in time is called a state vector (p). In general, the state vector changes in response to system events such as new user or doctor inputs and include such things as locale, month or any other input that would parameterize the system. In continuous systems, state vectors change constantly, but in discrete systems, state vectors change only a finite number of times. When at least one random variable is present, a model is called stochastic. When random variables are absent, a model is called deterministic. Sometimes the mathematical relationships describing a system are simple enough to solve analytically. Analytical solutions provide exact information regarding model performance. When the model cannot be solved analytically, it can often imitate system operations via simulation enabling performance to be estimated numerically.

Referring further to FIG. 3, there is illustrated a functional view of a system model 302 for the function y=f(x, p), where y is the output vector from the model, x is the input vector and p is the state vector. Systems are modeled as having a number of inputs based upon patient and doctor inputs that comprise an input vector $x=x_1, x_2, \ldots, x_r$; a number of outputs representing doctor (medical providers) rankings may comprise a vector $y=y_1, y_2, \ldots, y_s$; and a number of system state factors that comprise a state vector $p=p_1, p_2, \ldots, p_r$. Internally, the model can have various constants or weights that are varied during the training process, as will be described hereinbelow. Very different groups of patients and doctors each provide unique inputs that are unpredictable, and system parameters often arise as a means for tuning responses in some desired manner. Thus, inputs commonly are modeled as random processes, and system parameters as adjustable conditions. Thus, a system model is viewed as a function f( )_ that produces output y from inputs x and system parameters p; that is, y=f(x, p), as shown in FIG. 3. Modeling involves constructing an abstract representation based upon the choices of the patients and doctors. The model determines which system elements (in this case user and doctor choices) are essential and generates its weighting factors with respect thereto during training of the model. Basically, some inputs have no effect on the output. An example would be, for example, the color of the eyes for any particular patient. Even though this could be an input to the model, testing of the model at a later time by manipulating this input would more than likely show (depending upon the malady) that the resultant ranking would not change. Such later testing would show that the model is insensitive to this particular input and it could actually be eliminated from the input vector.

Figure 4:
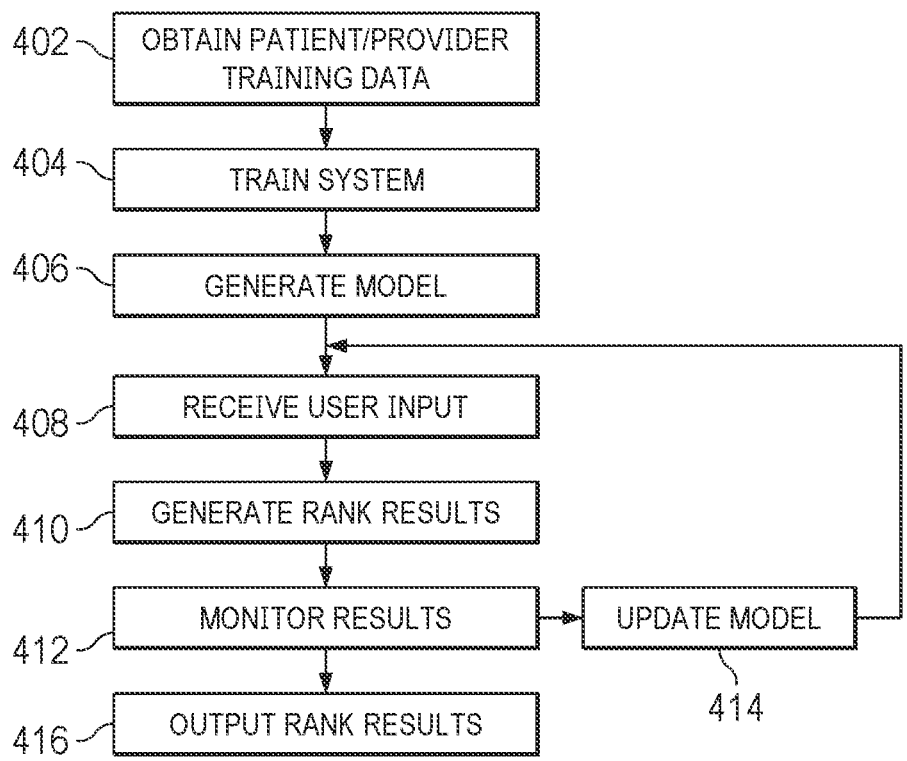
FIG. 4 illustrates a manner for generating and updating a system model.

Referring now to FIG. 4, there is more particularly illustrated the overall manner in which the system model 302 is generated and updated responsive to the receipt of additional result information. The process begins at step 402 wherein patient training data 107 and medical provider training data 109 are obtained. The more inputs received from different patients and medical providers, the better the system will model the behavior of the desires of patients and medical providers to provide better ranking lists. The training data is used to train the system at step 404. Training of the system involves the creation of a stored representation that defines the behavior of the patients and the medical providers and their preferences/rankings for each other. These determinations are made based upon the training data and used to generate an overall system model at step 406. Next, the trained system model receives data for an individual user input (requesting patient) at step 408. This information is provided to the generated system model to generate rank results at step 410. The rank results comprise a list of medical providers that is most likely to appeal to the requesting patient based upon the provided user input information as determined by the system model, this information being both desires of the patient and desires of the provider. The system, in addition to generating the rank results, monitors these results at step 412. The monitored results are used to determine if additional improvements may be made to the system model and, if necessary, the system model may be updated at step 414 which is then used for the generation of further rank results when additional user input is received at step 408. The output rank results are output to enable a requesting patient to select their doctor at step 416.

Figure 5:
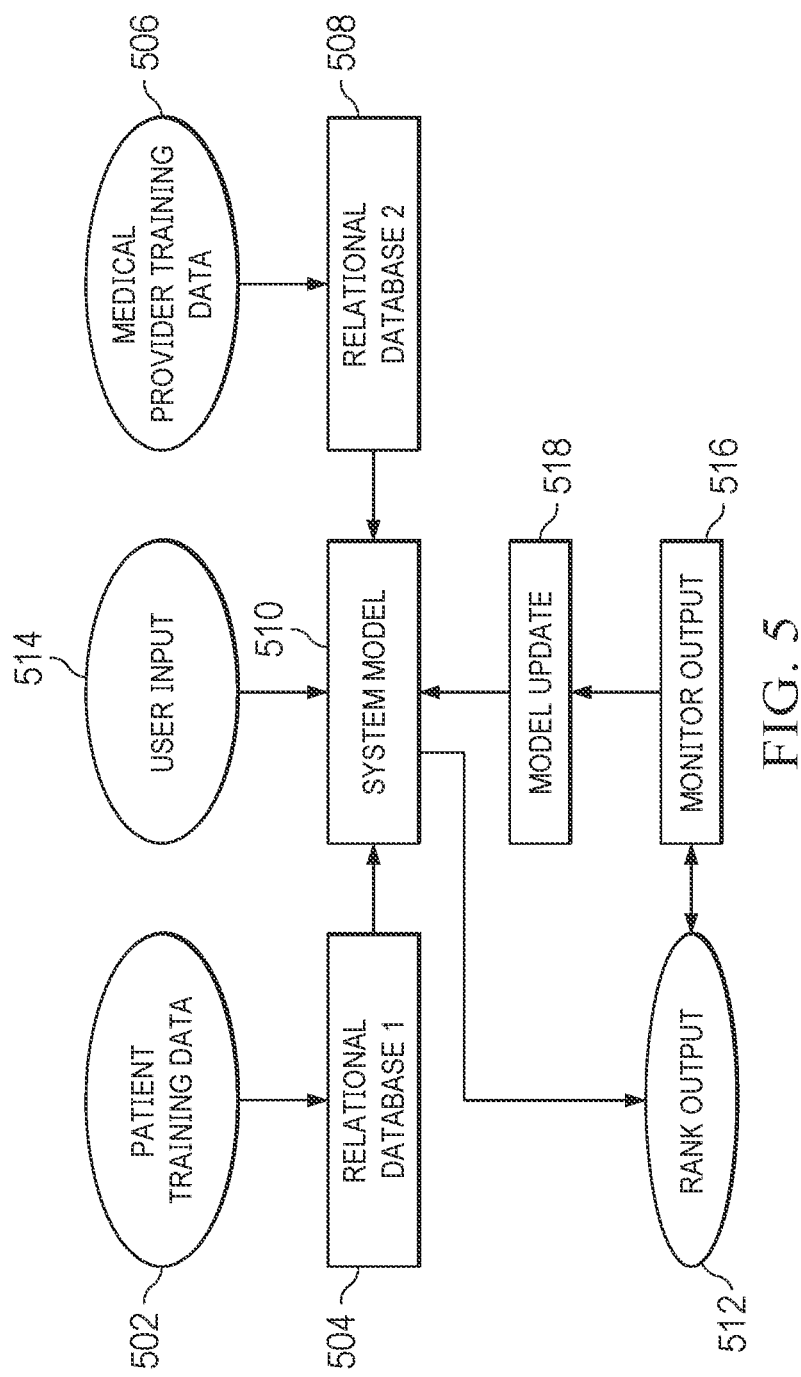
FIG. 5 illustrates a functional block diagram of a system for generating a model for ranking of medical providers based on system and patient data.

Referring now to FIG. 5, there is provided an overall functional block diagram of the system for generating a model that provides rank listings of medical providers based upon both patient data associated with the requesting patient and medical provider data associated with the available medical providers. Patient training data 502 is used for creating a first relational database 504 that includes information regarding all the trends and requirements associated with patient selections and preferences with respect to medical providers. While the following example describes a system using a relational database 540 other types of databases may be used such as a key-value database, document store database, graph database, or a variety of other database types. Similarly, medical provider training data 506 provides information from medical providers such as doctors, hospitals, nurse practitioners, nursing homes, rehab facilities, etc. that are used for the creation of a second relational database 508 that includes information regarding medical provider preferences with respect to patients and requirements. The information from the first relational database 504 and the information from the second relational database 508 are used for creating a system model 510. The system model 510 comprises a stored representation that is generated as described hereinabove and as more particularly illustrated with respect to FIG. 6.

Figure 6:
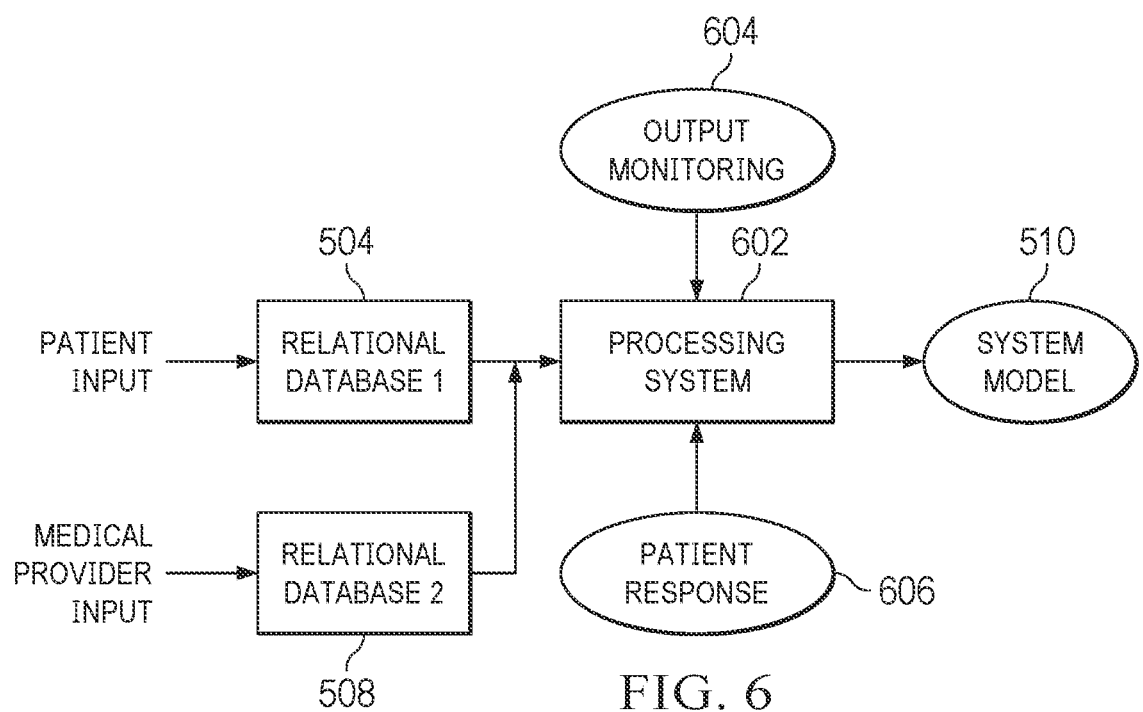
FIG. 6 illustrates the components for generating the system model.

FIG. 6 illustrates the components for generating the system model 510. A processing system 602 including learning functionalities enables the generation of a system model 510 that represents patient and medical provider preferences. The processing system 602 receives patient data from relational database "1" 504 that stores information with respect to the patient data that enables generation of the system model. This is the patient training data that contains preferences/rankings of medical providers by a plurality of patients for medical providers. Similarly, the medical provider data is provided from relational database "2" 508 that stores medical provided preference data for patients. This is the medical provider training data that contains preferences/rankings of patients by a plurality of medical providers for patients. The processing system 602 may also receive input parameters 604 that provide additional improvements to the system model 510 which may be provided by the processing system 602 responsive to patient satisfaction responses 606 of the output of the system model. The output of the system model 510 may be monitored for user or doctor biases that may be illustrated in the outputs, patient dissatisfaction with the outcome or the provided ranking list. If these types of trends are detected, the processing system 602 may correct the system model 510 to remove the relevant parameters that are associated with these trends. The processing system can remove biases by ignoring the input parameters that may reflect the detected biases. The mathematical formula of the processing system can detect the biases and account for this when providing the rank list outputs. The processing system can also ignore the particular inputs that may be contributing biases to an analysis. The processing system 602 may also update the system model 510 based upon patient responses 606. Further input can be received from a requesting patient based upon their feedback of medical provider selections or satisfaction with services received from a particular medical provider, this being new data that will update the patient training data 106. This feedback from patients who have used the system model for selecting a medical provider may detect further issues with the system model 510 and be used to update its mathematical formula to improve ranking outputs provided by the model.

The processing system 602 may comprise any number of learning systems that may be updated based upon newly received patient data and medical provider data. The processing system may use a variety of different techniques for generating the stored representation of the system. These techniques include, but are not limited to, neural networks, multilayer neural networks, linear regression analysis, random forest, XG Boost, linear regression techniques, linear engines, non-linear engine and other known techniques for generating a dynamic mathematical formula for describing or representing the selection system. It will be appreciated by one skilled in the art that various other types of learning systems that may modify a system model based upon a continuous stream of user inputs may be utilized.

Referring now back to FIG. 5, the system model 510 generates medical provider ranking outputs 512 responsive to a user input 514 provided by a particular user. Thus, the particular user will provide input information 514 responsive to a questionnaire or input template that is provided via some type of interface, in addition to any other information available that is necessary to define that user to the system, such as a medical history. The system model 510 receives these user inputs 514 and generates the rank output 512 which may then be displayed to the user that has provided the user input 514. The user may then make their selection based upon the rank output 514. The output of the system model 510 is also monitored by an output monitor 516. As discussed previously, this may be carried out by the processing system 602 and used to update the model at 518 based upon determinations made responsive to the monitored output.

Figure 7:
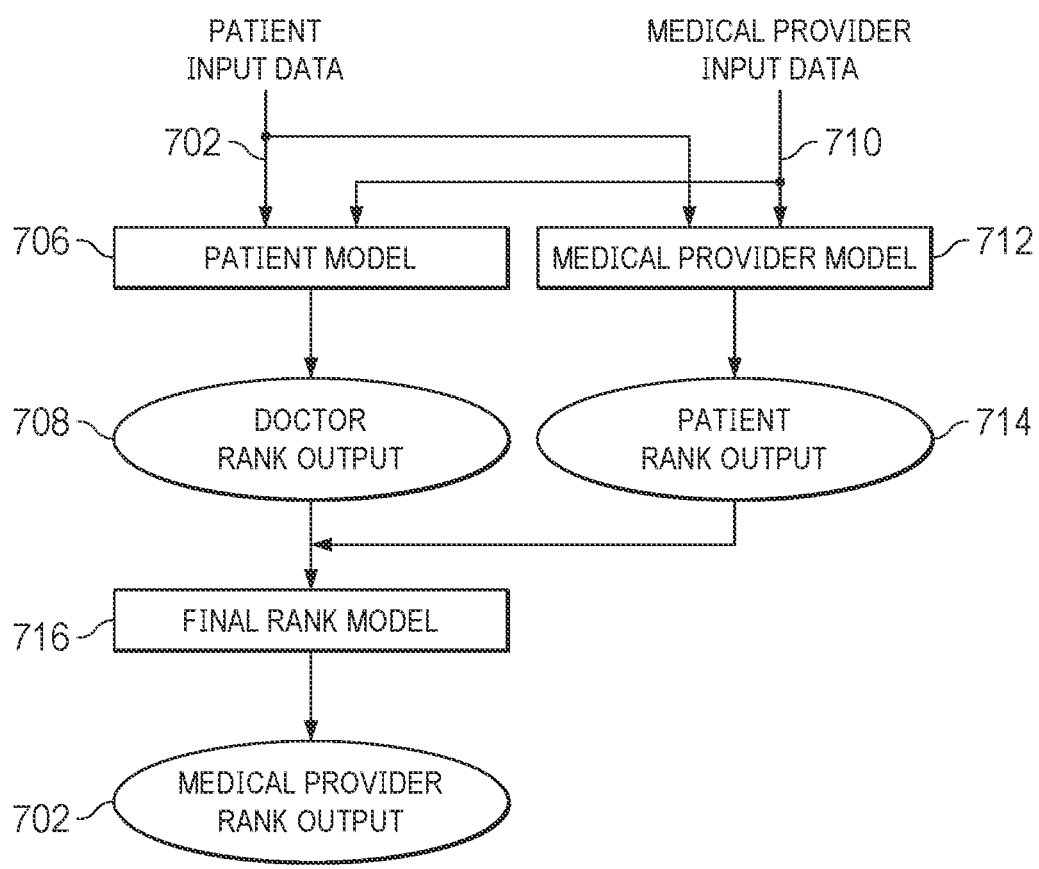
FIG. 7 illustrates the manner for processing information from relational databases by the system model.

Referring now to FIG. 7, there is illustrated the manner in which the system model 510 may process information from the relational databases 504 and 508 to determine a particular medical provider rank list output 702. Patient input data 704 are input to a patient model 706 that has been developed using the processing system 602 described previously. Data from a medical provider input data 710 is also input to the patient model 706. This data from the medical provider input data represents a data set of available doctors processed through the patient model 706. The patient model 706 will sequence through each of the available doctors in the medical provider input data 710. The patient model 706 then generates a medical provider rank output 708 that provides a ranking of each of the medical providers based upon the patient preferences indicated by their user input data 704 as processed by the patient model 706. Similarly, the medical provider input data 710 are provided to a medical provider model 712, as well as the patient input data 702 from the requesting patient. Medical provider model 712 generates a patient rank output 714 based upon each of the available medical providers desires for the particular patient or patient types corresponding to the individual patient or requesting patient represented by the patient input data 702.

In this operation, the request to the model for processing involves information from a particular individual or requesting patient represented by the patient input data 702. The medical provider input data 710 comprises a list of "available" medical providers. Thus, the patient model 706 is operable to receive information about each of the medical providers that are available and contained in the medical provider input data 710 in order to provide the doctor rank output 708 for each of the available medical providers in the medical provider input data 710 by sequencing through each of the available medical providers in the medical provider input data 710. For each available medical provider processed within patient model 706, the medical provider model 712 will provide an output representing how that particular available medical provider from the medical provider input data 710 in the sequence evaluates a patient similar to the requesting patient. Thus, the medical provider model 712 receives input from the patient input data 702. Thus, the overall model must process each available medical provider for both the patient model 706 and the medical provider model 712 to determine the corresponding doctor rank output 708 and the patient rank output 714 for that particular medical provider.

A final ranking model 716 provided by the processing system 602 utilizes the medical provider rank output 708 for all of the available medical providers processed from the medical provider input data 710 and provided on the output of the patient model 706 and the patient rank output 714 for all of the available medical providers processed from the medical provider input data 710 and provided on the output of the medical provider model 712 in order to determine a final medical provider rank list 716 based upon both the patient desires and the medical provider desires. The final rank list model 716 utilizes a combination of patient desires and medical provider desires in order to provide a list that provides an optimal ranking of available medical providers to a patient that are most likely to meet the needs of all parties involved and provide a best medical provider list for selection by the patient.

Figure 8:
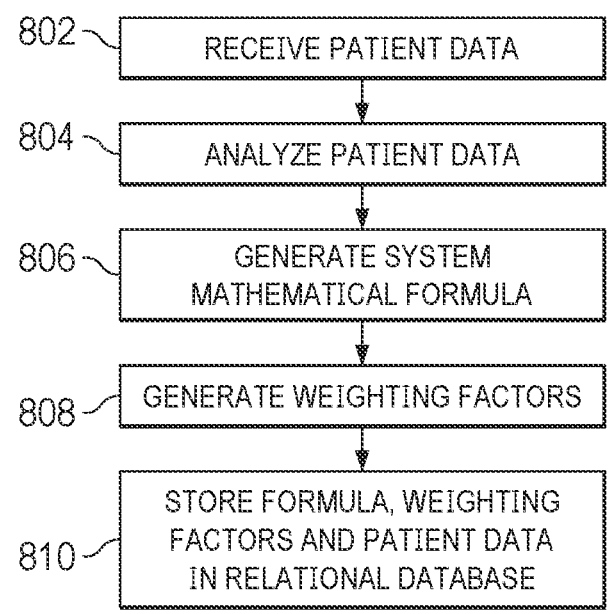
FIG. 8 illustrates the manner for generating a stored representation of a system.

Referring now to FIG. 8, there is more particularly illustrated the manner in which the processing system 602 of FIG. 6 would generate the stored representation with respect to the patient preferences for generation of a patient preferences output rank list. The patient training data is received at step 802. As discussed previously, the patient training data would comprise a plurality of inputs from different patients indicating their preferences, demographic information, medical condition, patient medical statistics, etc. The patient data is analyzed by the processing system 602 at step 804. Based upon this analysis, a system stored representation is generated at step 806 with respect to ranking physicians based upon solely patient information. Various weighting factors used within the stored representation are generated at step 808 based upon the provided patient training data. Thus, for example, if a particular weighting factor was associated with selection preferences based upon a patient's age, then the age of the patient would be provided with a greater weighting factor than a weighting factor that was shown to have very little bearing upon a patient's choice of medical provider. After the weighting factors have been created the weighting factors and patient data are then stored within the relational database 504 at step 810.

Figure 9:
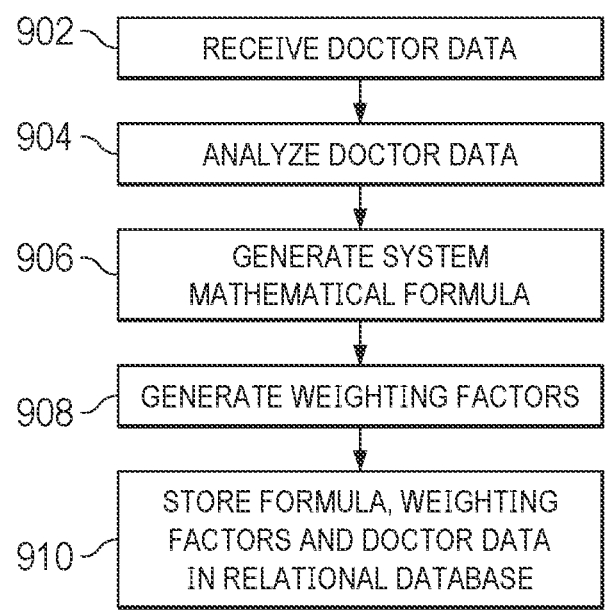
FIG. 9 illustrates more particularly the manner for generating the stored representation of the system.

Referring now to FIG. 9, there is more particularly illustrated the manner in which the processing system 602 of FIG. 6 would generate the stored representation with respect to the medical provider preferences for generation of a medical provider preferences output rank list. The medical provider training data is received at step 902. As discussed previously, the medical provider training data would comprise a plurality of inputs from different medical providers indicating their preferences, medical specialties, patient medical statistics, etc. The medical provider data is analyzed by the processing system 602 at step 904. Based upon this analysis, a system stored representation is generated at step 906 with respect to ranking patients based upon solely medical provider information. Various weighting factors used within the system are generated at step 908 based upon the provided medical provider training data. Thus, for example, if a particular weighting factor was associated with selection preferences based upon medical provider's practice area, then the practice area of the medical provider would be provided with a greater weighting factor than a weighting factor that was shown to have very little bearing upon a medical provider's patient choice. After the formula and weighting factors have been created the generated formula, weighting factors and patient data are then stored within the relational database 506 at step 910.

Figure 10A:
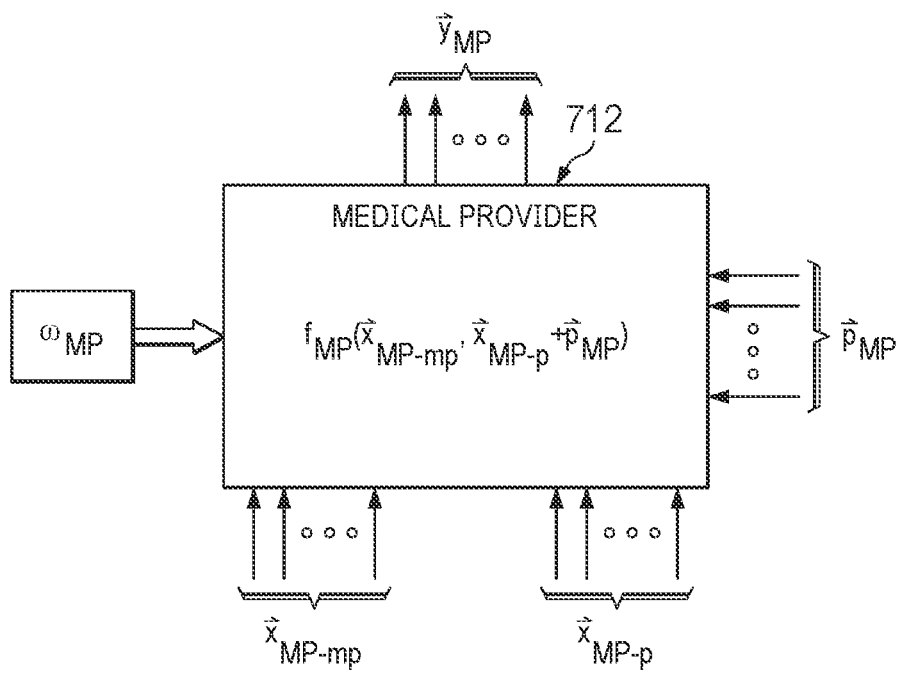
FIGS. 10A and 10B illustrate the medical provider and patient models.
Figure 10B:
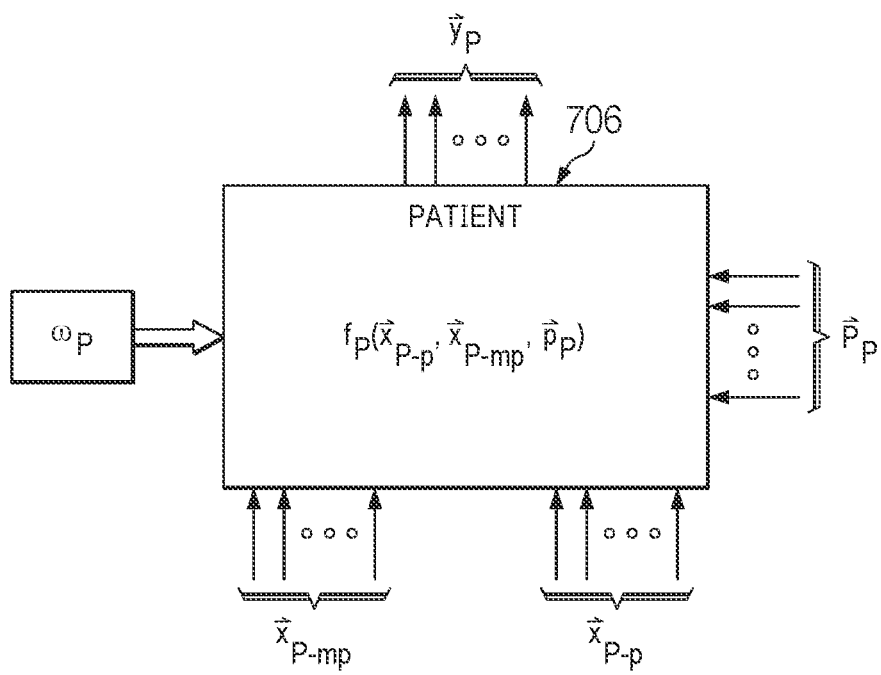

Referring now to FIGS. 10A and 10B, there illustrated diagrammatic views of the respective medical provider model 712 and patient model 706 for modeling the respective preferences thereof. As described hereinabove, each of the medical provider and the patient have different factors that enter into a preferential selection of the other.

With specific reference to FIG. 10A, the medical provider model 712 is operable to receive two vector inputs. The first vector input is the vector $x_{MP-mp}$ representing a plurality of information that is associated with medical providers and a vector $x_{MP-p}$ representing a plurality of information that is associated with patients. Each of the inputs associated with these vectors can be any type of information that will be uniquely associated with either a medical provider or a patient. For example, the information associated with vector $x_{MP-mp}$ for the medical provider will be such information as their education, gender, etc. But it should be understood that this could be any information associated with that individual even the type of music they like. Some information can be relevant and some irrelevant to a preferential decision with respect to the creation of the models as will be described below. This is the same with respect to the patient information. The model 712 is operable to provide a prediction by mapping the two vector inputs $x_{MP-mp}$ and $x_{MP-p}$ through a stored representation of a preference prediction system. This utilizes a model that is trained on a statistically significant amount of medical provider data and patient data in addition to associated medical provider preferences relative to that patient data. The medical provider preferences can be based on patient characteristics and use of "satisfaction" scores to drive the training of the model. Thus, the output of the model 712 is a vector $y_{MP}$ representing a group of different medical provider preferences. These preferences are determined, for example, by determining preferences from a group of medical providers that are utilized for the training operation that expressed certain preferences based upon multiple patients represented by information in the vector $x_{MP-p}$. These preferences could be such things as how many questions the patient asks, how compliant a patient is, how knowledgeable a patient is about their malady, etc. These are things that a medical provider might use in ranking a patient as desirable or undesirable. In addition to the vector inputs representing medical provider information and patient information, there are also provided state inputs in a vector $p_{MP}$, which represents state information about a particular model at any given time. Such state information might be the time of the year, the day of the week, etc. The model 712 is thus represented by a function $f_{MP}(x_{MP-mp}, x_{MP-p}, p_{MP})$, where the input vectors are mapped through this function to the output to provide the prediction $y_{MP}$. The training of this network will be described herein below. Once trained, the network will have associated therewith a plurality of weights comp that represent weighting factors that can be varied during the training of the model. These weights basically define the relationship embodied in the function $f_{MP}(\ )$ between any one of the inputs in a particular vector and any one of the outputs in the output prediction. As noted hereinabove, any amount of information or any type of information about a particular medical provider or a patient can be included in the associated medical provider or patient vector. Some of these inputs may be quite relevant to any decision regarding a preference and some may be quite irrelevant. For example, if information regarding a patient's preferred diet preference, such as vegan, were included as an input in the patient vector $x_{MP-p}$, it is unlikely that this information would have any influence on the output. Thus, the model would assign a relatively low weight to the relationship between this input and the prediction provided by the model. One could see this by, for example, once the model is trained, varying this input and observing that the prediction remained the same. Typically, these are called insensitive inputs and they can actually be eliminated from the vector with no detrimental effect on the training of the model and the confidence in the prediction.

With specific reference to FIG. 10B, there is illustrated a diagrammatic view of the model 706 for the patient side of the overall system. This is constructed similar to the model 712 in that there is provided information regarding the medical providers and information regarding the patient. The vector inputs for the medical are provided by a vector $x_{P-mp}$ and for the patient by a vector $x_{P-p}$. The various inputs that form the vectors could be identical to the two input vectors for the medical provider model 712 in that they contain a lot of information. However, each of the medical provider model 712 and the patient model 706 may have certain inputs relevant to one and not to the other in predicting the respective preferences. To determine preferences related to a desired patient for a medical provider, one relevant input might be the ability to pay their bill. From the patient's side of the decision-making process, one relevant input might be the athletic background of that medical provider. Both of these inputs are not required for both sides of the decision-making process. But including them just as additional inputs is not detrimental to the overall model.

The patient model 706 also includes a state vector $p_P$ defining certain states of the model and a plurality of weights $\omega_P$ parameterizing a function $f_P(x_{P-mp}, x_{P-p}, p_P)$, this function representing the stored representation of the patient preference, through which the two input vectors are mapped to provide an output vector $y_P$. This output vector represents a plurality of outputs associated with certain preferences. For example, patients may be queried to rate a medical provider with such things as bedside manner, ability to provide a follow-up call, ability to clearly explain in non-medical language the medical situation, etc.

Figure 11:
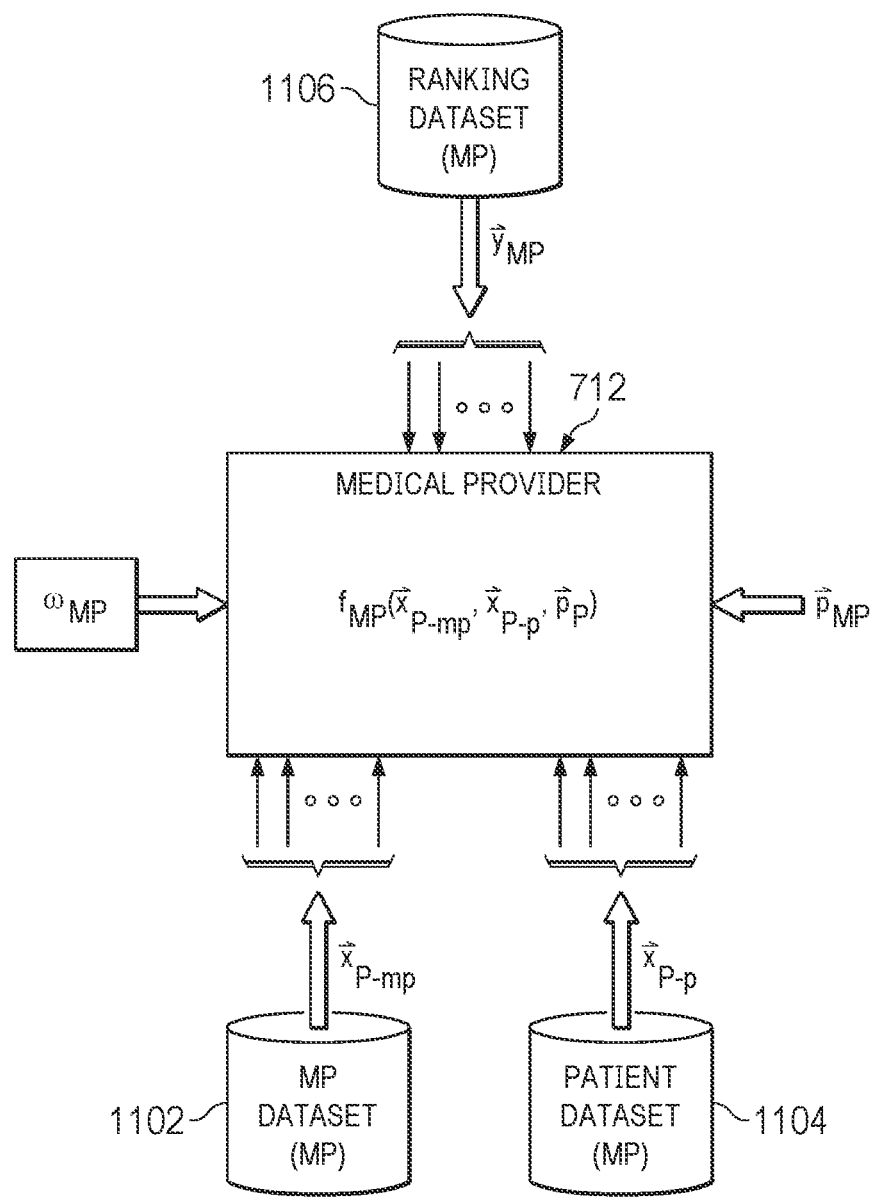
FIG. 11 illustrates a diagrammatic view of the medical provider model in a training mode.

Turning now to FIG. 11, there is illustrated a diagrammatic view of training operation for training the medical provider model 712. Depending on the type of model utilized, medical provided data from a medical provider data set 1102 is provided for the input vector $x_{MP-mp}$ and patient data is provided from a patient data set 1104 for the input vector $x_{MP-p}$. There is also provide a ranking data set 1106 that provides training data for the output vector $y_{MP}$. The ranking data set 1106 is a relational database associated with medical provider data set 1102 and the patient data set 1104. Thus, a plurality of medical providers will provide information in the form of preferences or rankings for a particular patient in the patient data set 1104 and these will all be related to each other. In a typical training operation, an iterative approach is followed, but this is dependent on the architecture of the model employed. Again, this disclosed embodiment is not to be considered limiting in any way. The model could be a linear model, a nonlinear model or other such model.

In the exemplary model disclosed herein in one embodiment, an iterative approach is employed wherein inputs from the medical provider data set 1102 and patient data set 1104 are provided as inputs as well as the correlating and associated preference data. The weights comp associated with the function $f_{MP}(\ )$ are then incrementally adjusted based on the values of the various inputs. If, for example, 90% of inputs had a null value and the remaining of the inputs had a non-zero value, these inputs would be known as influencing the model. If, for example, for a particular medical provider who ranked a particular patient and there were four preferences ranked on a scale of 0-10 as 3, 5, 2, 9, respectively, the relationship between that 10% of the inputs and those values would be reflected in the incremental change in the weights $\omega_M$. If this relationship continued for different medical providers and different patients, it would be a strong relationship. Thus, the training operation would involve selecting a medical provider and the associated preferences for a plurality of patients. The next medical provider would be selected and the weights of the model 712 adjusted for the current medical provider's preferences each for a given one of the plurality of patients. It would be expected that any particular medical provider would have an associated set of inputs that was unique thereto and formed a vector $x_{MP-mp}$ associated with that medical provider and each of the different patients that was ranked as to preferences by that medical provider would also have an associated set of inputs that was unique to that particular patient and formed a vector $x_{MP-p}$. However, medical providers and patients are defined in general by the value of the various information stored in data sets 1102 and 1104. It is just that each medical provider and each patient have different values for those inputs that define the various vectors. This example assumes a traditional training/modeling approach. Other types of system that use for example deep neural networks as referenced herein may also be used to prioritize the medical provider listing.

From a training perspective, the more data that is available, the better the prediction. The quality of the prediction is sometimes referred to as a confidence factor in the prediction. This, of course, is based on the quality of the data set upon which the model is trained. The confidence factor of any model increases if the model is trained on a fairly dense data set. However, any data set could be considered to be sparse in certain areas of the data set. For example, if the patient data in a particular data set focused on patients in North America but the requesting patient utilized for the prediction providing medical information actually came from the outback of Australia, the confidence level in the prediction might be lower due to the fact that the model was not trained on a data set from a population that included this particular patient. However, any model will still make a prediction based upon the input data, albeit at a lower confidence level.

The patient model 706 is trained in the same manner as the medical provider model 712 and utilizes a medical provider data set 1102', as will be described hereinbelow with respect to FIG. 15, providing information associated with the input vector $x_{P-mp}$, and a patient data set 1104' associated with the input vector $x_{P-p}$. These data sets 1102' and 110' are actually separate data sets from the data set 1102 and the data set 1104 because the medical provider data set 1002' and patient data set 1104' have an association with a separate patient ranking data set 1106' for the vector $y_P$, thus requiring different medical provider and patient data sets. This is because a particular patient will rank a particular medical provider having associated information in the separate medical provider data set 1102'. The training would require incrementing through information of a particular patient and all of their associated medical providers and the ranking that particular patient provided for each of those associate medical providers. The training utilizes all of the information associated with that particular patient and a particular medical provider associated with a particular ranking. Once all of the medical providers that had a ranking provided for by a given patient is complete, the next patient would be selected. During this incremental training, the weights ow for the patient model 706 would be modified to reflect the changes and the effects that certain inputs have on the output. Then the procedure will be repeated for the other patients in the data set 1104'.

Referring now to FIG. 12, there is illustrated a tabular representation of the input vector $x_{MP-mp}$ in the medical provider data set 1102 that defines various attributes of medical providers. This is by way of example only. In this tabular representation, the medical providers are represented by the values 01, 02, 03, . . . , n. By way of example and not by way of exhaustion, certain attributes that may be of interest with respect to information provided to the model for modeling a medical provider's preference for a patient would be such things as their practice area, their gender, their age, their ethnicity, their location, their experience, their insurance plan and even possibly their religious affiliation. For these data sets 1102 and 1104, they are used for training of the medical provider model 712. As such, they are relational data sets in that each medical provider has an association with each patient defined by the ranking, i.e., they have interfaced with that patient and have provided some ranking of some sort. This is different when compared, as described below, with data sets utilized for generating predictions. The content of the information input can, and will more than likely, be different in the operational mode as compared to the training mode, but the type of input or the type of attribute will remain the same for any given input vector. Any amount of information that can be provided in some type of profile for a particular physician or medical provider can be utilized as an input for the vector $x_{MP-mp}$. Even if it is superfluous information, such as possibly the type of diet a particular medical provider prefers, such information might influence or affect the model. As noted above, if an input has no effect on the predicted output, it is just a variable to which the prediction provided on the output of the model has no sensitivity. However, even an insignificant detail or attribute relating to any medical provider, when considered over thousands of individuals that are utilized in the training operation of the model, can have an effect on the predicted output.

Referring now to FIG. 13, there is illustrated a tabular representation of the input vector $x_{MP-p}$ in the patient data set 1104 that defines various attributes of patients. This is by way of example only. In this tabular representation, the patients are represented by the values A, B, C, . . . , m. By way of example and not by way of exhaustion, certain attributes that may be of interest with respect to information provided to the model for modeling a medical provider's preference for a patient would be such things as their age, their gender, their ethnicity, the type of malady that may be involved, their weight, their location, their income bracket and possibly their religious affiliation. These are broad categories as, for example, a particular malady could be comprised of multiple inputs, one for each potential malady.

Referring now to FIG. 14, there is illustrated a tabular representation for the output vector $y_{MP}$. As described hereinabove, this particular output vector is represented as a plurality of particular preferences. These preferences may have been determined to be those that are important when a medical provider evaluates a particular patient. Thus, the medical provider model 712 models each of these particular preferences, i.e., there will be a separate prediction for each of these preferences based upon mapping through the model 712 the inputs from a given medical provider regarding particular attributes therefor and inputs from a given patient regarding particular attributes therefor. By way of example and not by way of exhaustion, such things as temperament, compliance, honesty, appearance, how talkative the patient is, their intelligence, their knowledge of their health and their possible condition and possibly their religious affiliation could be considered to be important preferences to separately predict in order to determine ranking of different patients by the model. But it should be understood that a single ranking value could be provided by the medical provider for a particular patient. What this particular tabular representation comprises is data within the ranking data set 1106 that is utilized for training. Thus, for each medical provider, there will be a ranking provided for each patient that has interfaced with a given medical provider which has been ranked by that medical provider. This particular data can be then utilized as an input for training. Once trained, these particular preferences constitute the output of the model.

Figure 15:
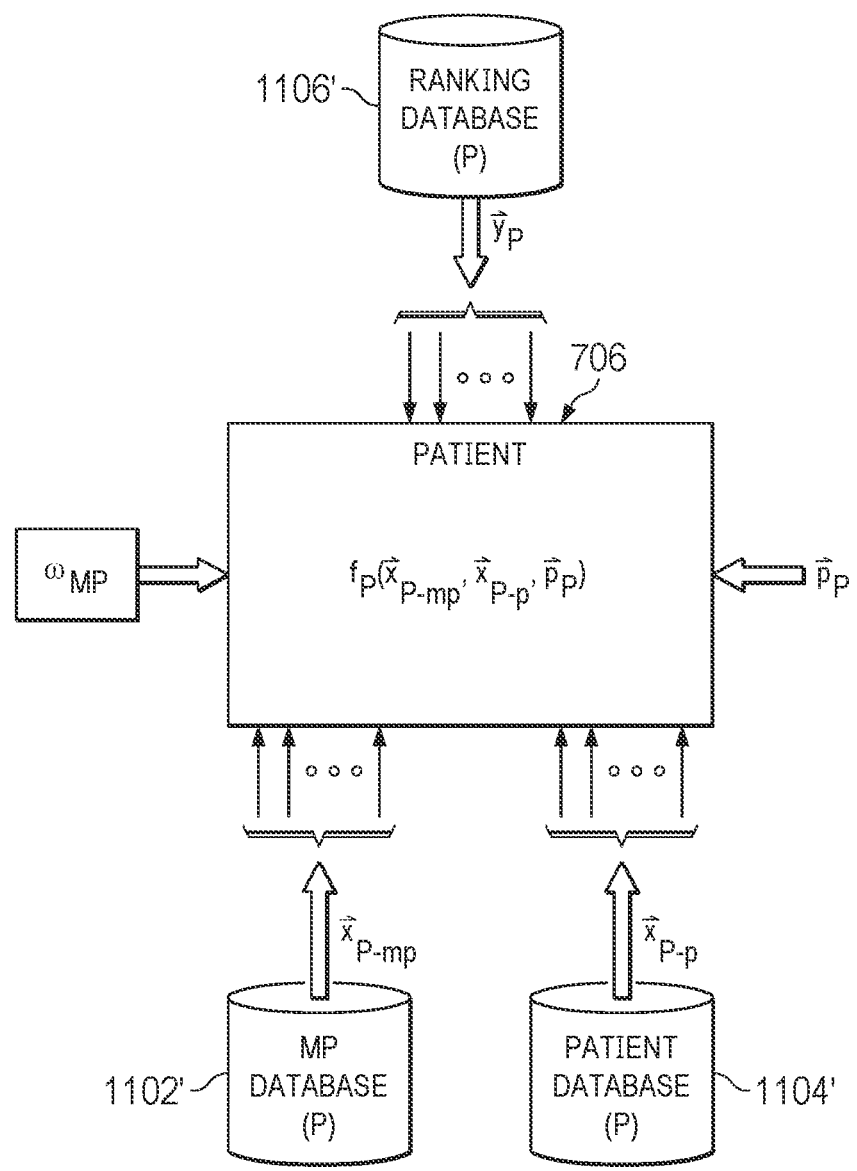
FIG. 15 illustrates a diagrammatic view of the patient model in a training mode.

Referring now to FIG. 15, there is illustrated a diagrammatic view of the patient model 706 during training. This training operation is substantially similar to that associated with the training of the medical provider model 706, described hereinabove with respect to FIG. 11. There is provided a medical provider data set 1102' and a patient data set 1104'. These can be the same as the medical provider data set 1102 and the patient data set 1104. The main difference is that the attributes associated with the vectors $x_{P-mp}$, $x_{P-p}$ are different than that associated with the vectors $x_{MP-mp}$, $x_{MP-p}$. It is possible that the attributes could be identical for all of the patient vectors and the medical provider vectors for the training operation of both of the model 706 and 712, but it should be understood that a number of the attributes that are relevant to the training operation of each of the models can be different. This just means that an attribute such as "office hours" would be an important attribute to a patient in determining the preference for a given medical provider and would be virtually insignificant in the decision-making process on the part of a medical provider. But, in the operational mode, all of the inputs for the both of the input vectors $x_{MP-mp}$ and $x_{P-mp}$ would have to be included for the medical provider input data 710 to both of the patient input model 706 and the medical provider model 712 of FIG. 7.

The total input vector from the medical provider input would be a combination of both vectors, but only the subsets $x_{MP-mp}$ and $x_{P-mp}$ need to be input to the respective models 712 and 706.

In the training process for training the model 706 to store a representation of the preferences of patients for medical providers, it is necessary to select a given patient within the data set 1104' and then incrementally select data from the medical provider data set 1102' for which a ranking exists within the ranking data set 1106'. Thus, the data in all of the data sets 1104', 1102' and 1106' are stored in a relational manner. The model 706 during training will receive as inputs the information about a given patient, information about a given medical provider with which the given patient has been interfaced in a medical capacity and a ranking the given patient has provided for the given medical provider. All of the medical providers with which the given patient has been interfaced and their associated rankings will be incremented through in the training operation. Thereafter, another given patient will be selected, and the process repeated. During this training process, each selection will incrementally modify the weights $\omega_P$ for the model 706. As noted hereinabove, the weights define the constants associated with the representation of the model. Depending upon the architecture selected for realizing the model, these could just be constants in a mathematical equation.

As noted hereinabove, these data sets 1102', 1104' and 1106' are training data sets. These training data sets contain information that was derived from patients that interacted with various medical providers. However, the output or the ranking is provided by the patient. This is to be compared with the training of the medical provider model 712 and the associated data sets 1102, 1104 and 1106, wherein the output stored in data set 1106 is provided from information that was received from the medical provider relative to their interaction with patients. Although there may be some overlap between patients and medical providers in the various data sets, the data sets 1102 and 1102' as well as the data sets 1104 and 1104' would typically be independant and separate data sets.

Referring now to FIG. 16, there is illustrated a tabular view of the medical provider data set 1102' for training the model 706. This data set will contain some value for the various attributes that are defined in the vector $x_{P-mp}$ for a group of medical providers. The medical providers are listed along the top axis as medical providers 01, 02, 03, . . . , n, and the attributes are listed along the side axis. In this exemplary set of attributes, such things that might be relevant to the preferences of a patient regarding attributes of a medical provider are such things as the practice area specialty, their subspecialty, their gender, their age, their ethnicity, any potential legal actions that may have been taken against the medical provider, what type of insurance they take, payment terms, potential religious affiliations, their location, their office hours and even their online ratings. There is basically no real limit to how many different attributes of any medical provider that might be relevant to how a patient perceives a particular medical provider. This perception is what is important in forming a preference for any particular medical provider.

Referring now to FIG. 17, there is illustrated a tabular view of data contained in the patient data set 1104' for the vector $x_{P-p}$. This data provides information on a particular patient. Again, each particular patient has a relationship with respect to these data sets 1102', 1104' and 1106' that is unique to each given patient, as each given patient has an actual relationship to an interface with each particular medical provider in the data set 1104' to which a ranking is provided, which is stored in the data set 1106'. The various attributes of a particular patient are provided as inputs within the vector $x_{P-p}$ that are useful in training the model 706, as the representation in the model 706 can be biased or influenced by any one or more of these particular attributes. The attributes that are set forth in this particular tabular representation, by example only, are things such as, as it relates to patient, age, gender, medical profile, weight, location, income bracket, potential religious affiliation and particular activities that that particular individual might be involved in, such as being athletic or the such. This is basically a fairly detailed medical profile of the particular patient. Since this data represents an actual interface between a medical provider and given patient, the information provided in the input vector might also include such things as the particular medical condition that was involved. For example, a male athlete that is seeking treatment for a knee injury will provide information to the model during training that was important to reflect preferences. If the male athlete were a baseball player, that male athlete might prefer a male medical provider having a specialty in orthopedics and who specifically specialized in knees and that possibly played baseball in their younger years. The fact that the preference of the patient was for a male medical provider with an orthopedic background specializing in knees and that had a baseball background, and the fact that the patient was a male with a knee injury from baseball could be important in order to provide a better trained model of patient preferences. If, after the model 706 was trained, a new patient was to input information into the model indicating that they too had a knee injury from baseball, one would expect a high ranking for a male orthopedic medical provider that specialized in knee injuries and that had an athletic background specifically in baseball.

Referring now to FIG. 18, there is illustrated a tabular view of the data set 1106'. As noted hereinabove, this particular data set 1106' is for training purposes in that it represents actual ranking information or preference information provided by a given patient for a given medical provider with which that given patient has interfaced at one time, i.e., this is an actual experience that was utilized to yield information about the preferences. As was the case for the medical provider model 712 training, this could just be a single ranking value from 0-10. In this particular example, there are provided a plurality of preferences that might be important to a patient as to how they perceive a given medical provider. These are exemplary only and not exhaustive. As an example, it might be such things as the bedside manner of the medical provider, how informative the medical provider was as to explaining a medical condition, how timely the medical provider is, i.e., how long it took to get the appointment or how long the patient had to wait in the waiting room, how thorough a particular medical provider was, again from the perception of the patient, gender of the medical provider, overall personality, the ability of a medical provider to follow up with the patient and communication in general. Consider the situation, for example, where a physician were to examine a child. If a first physician came in and examined a child in a very thorough and professional manner with the parent present, but never spoke a word to the parent or the child and just did their job and left, that would leave the parent with a perception about that particular physician. If a second physician then came in and spent a large amount of time with the child and was very communicative with both the parent and the child but never actually but their stethoscope in their ears, that will leave a different perception with the parent. More than likely the parent would be of the mindset that this second physician did a very thorough job and never noticed that the stethoscope was laying on the physician's shoulders. The perception that the parent has with respect to both of these physicians is distinctly different and quite subjective.

As noted hereinabove, these particular preferences set forth in this particular tabular view of data set 1106' are preferences that might be obtained by a later survey that was filled out by the given patient. As such, a given patient having had experience with a given medical provider would be provided a survey wherein they would rank each of the preferences set forth in the tabular list in FIG. 18 on some scale. There could, of course, be any number of preferences in the survey, but a typical survey needs to be short in order to be effective. The survey could merely be just a ranking of the medical provider, which would be simple. By providing a plurality of factors or preferences, a higher level of granularity can be achieved. A final rank can be provided by some algorithm to average all of these preferences.

Figure 19:
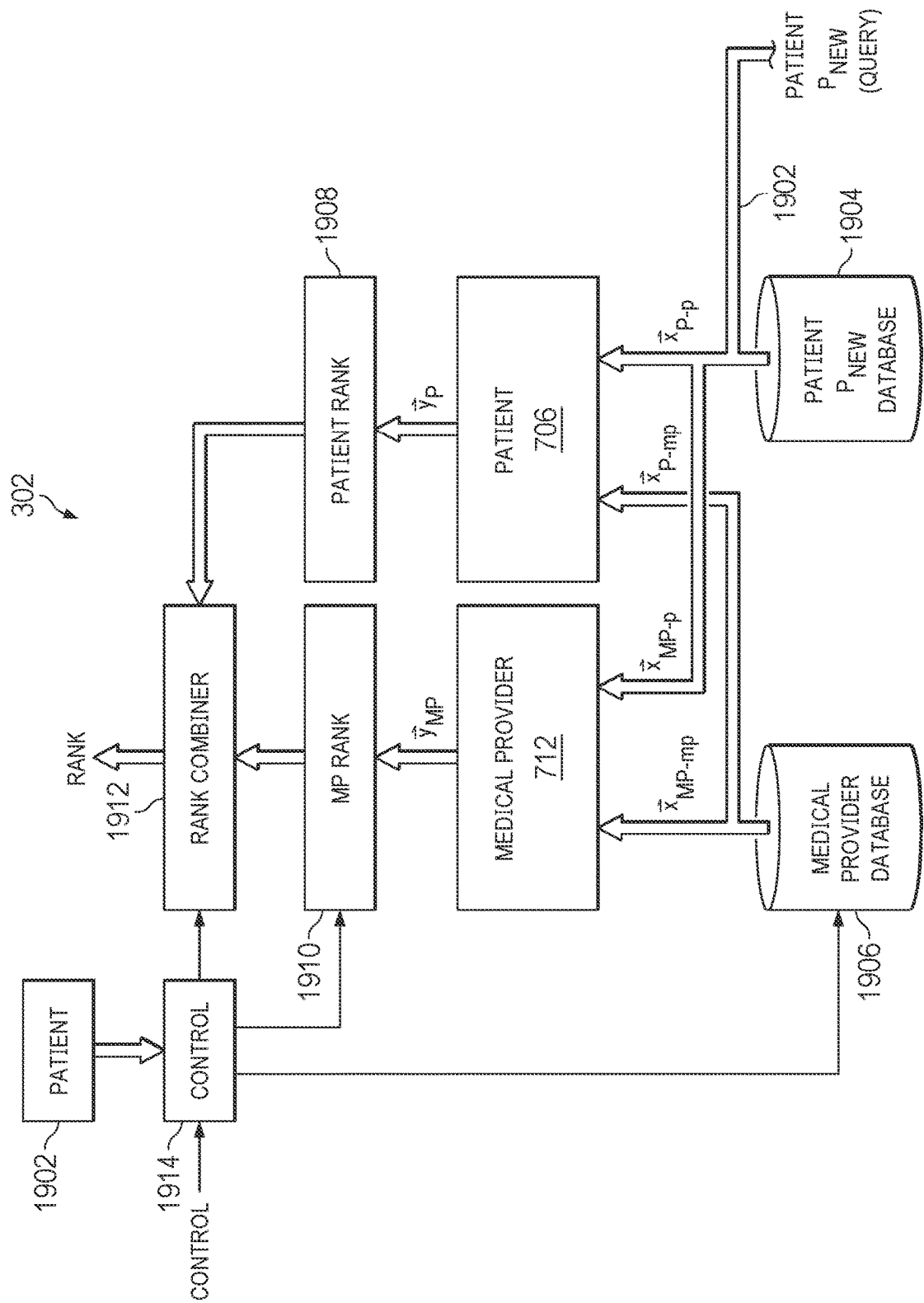
FIG. 19 illustrates a diagrammatic review of the overall system model for generating a Rank in response to a new patient's $P_{NEW}$ query.

Referring now to FIG. 19, there is illustrated a diagrammatic view of the overall system model 302. This diagrammatic view illustrates the operation of the system with fixed system parameters, i.e., the weights thereof are fixed via the training operation. In the operation, a new patient 1902 will first enter the system with a request for a medical provider. This new patient has certain information associated therewith and this is represented by a patient data set 1904. It should be understood that this patient data set 1904 just merely represents a data set from which information regarding this particular patient may be stored. For example, this patient may already be a patient within the data set of a facility or in the system, and certain information regarding that patient that is relevant to the inputs in the vectors $x_{P-p}$ and $x_{MP-p}$ is extracted from this data set 1904 for input to both of the models 706 and 712. There can be other additional information that is provided, such as information regarding the particular malady or medical condition the patient is inquiring about, the type of medical provider that the patient is seeking, etc. This is not typically information that will be included in a patient profile. Information included in a patient profile would be information that would be normally stored in the patient data set 1904. Of course, if the patient had never been in the data set, such profile could be created. The information from the patient 1902 and the associated patient data set 1904 is information required to digitally convert the patient to a vector input. As described herein, each of the models 706 and 712 receives as an input information about the patient via vectors $x_{P-p}$ and $x_{MP-p}$ and these vectors are each comprised of a plurality of input values. They could possibly be identical or different. Additionally, it may be that a particular patient has not provided enough information to provide values for the full vectors $x_{P-p}$ and $x_{MP-p}$, and those values will then be a nullity. But each of the models 706 and 712 operates independently of the other such that all that is required in the information from the patient 1902/patient data set 1904 is enough information for the models 702 and 706 to provide an output with an acceptable confidence level.

Additionally, there is provided a medical provider data set 1906 which contains information about available medical providers in the "system." This medical provider data set will provide the information necessary for the medical provider input associated with the vectors $x_{P-mp}$ and $x_{MP-mp}$ for input to both of the models 706 and 712. As was the case with the patient, this information digitally converts each medical provider in the data set 1906 to a vector input for the vectors $x_{P-mp}$ and $x_{MP}$. As noted above, each of these vectors $x_{P-mp}$ and $x_{MP-mp}$ can have a different set of values of which some overlap. The respective models 706 and 712 are, in the training operation, trained, in one disclosed embodiment, on select ones of these values and, correspondingly, in the operational mode operated on the same set of values. For example, the value associated with payment terms for a medical provider may be important for the training of the patient model 706 but insignificant for the training of the medical provider model 712. Thus, it need not be input to the medical provider model during operation. However, from a normalization standpoint, it is possible that all of the values for the vectors $x_{P-mp}$ and $x_{MP}$ from the medical provider data set 1906 could be the same for both models 706 and 712, and all of the values for the vectors $x_{P-p}$ and $x_{MP-p}$ from the patient data set 1904 could be the same. Each of the models 706 would 712 would ignore input values in the respective input vectors that had no effect on the output. This normalization, although a possibility, would not improve the training operation and would not necessarily be desirable.

During operation of the model 302, a prediction is provided on the output of both of the models 706 and 712. The patient model 706 will provide a predicted preference for a particular physician. Thus, the patient model 706 will provide a medical provider preference prediction for each medical provider in the data set 1906. For this operation, a filter will typically be employed, as there is no need to predict a medical provider preference prediction for a medical provider in the infectious disease area when a patient is looking for a medical provider in the orthopedic area for a sore knee. Additionally, the data set 1906 could be limited to only those available medical providers within a certain locale. However, the system can provide a predicted preference from the model 706 for all of the available medical providers, no matter how large the data set 1906. This prediction by the model 706 does not reflect what the patient 1902 prefers; rather, what it predicts is what a large number of patients having a similar set of values for the patient input vector $x_{P-p}$ determined as a preference for a medical provider having a similar set of values for the medical provider input vector $x_{P-mp}$. It may be that a particular patient and a particular medical provider both having their information digitally converted to vector values had never been interfaced with the system before. The model 706 will still provide a prediction of a preference for that medical provider by that patient.

During operation of the model 302 on the medical provider side, the model 712 will provide as an output a patient preference prediction based on the input from the patient side and the information provided by the selected one of the available medical providers from the data set 1906. Thus, even though the information from the patient input vector remained the same for each prediction, there will be a patient preference prediction for each medical provider for that patient vector that also has a corresponding medical provider preference prediction provided by the model 706. As was the case with the operation of the model 706, this prediction by the model 712 does not reflect how the selected one of the medical providers ranks as to a preference the patient 1902; rather, what it predicts is what a large number of medical providers having a similar set of values for the medical provider input vector $x_{MP-mp}$ determined as a preference for a patient having a similar set of values for the patient input vector $x_{MP-p}$. It may be that a particular patient and a particular medical provider both having their information digitally converted to vector values had never been interfaced with the system before. The model 712 will still provide a prediction of a preference for that patient for that medical provider.

On the patient side associated with the model 706, the preference prediction associated with the vector $y_P$ is further processed to determine a single rank value for all of the predicted preferences, as set forth in the example of FIG. 18. This can be some type of averaging operation or the like. This is performed by a rank calculator 1908. Similarly, on the medical provider side, a patient rank will be provided by a rank calculator 1910. These rank calculators 1908 and 1910 convert or normalize all of the predicted preferences to a single value. This is by way of one example in the disclosed embodiment, as it is also possible to make decisions based upon all of the predicted preferences.

The ranking process is asymmetric between the patients and the medical providers. The patient preferences and the medical provider preferences are based upon unrelated data based upon the different interests between the patients and the medical providers. These asymmetric interests are each considered by the rank combiner in determining the final ranking prioritization. The output of both of the rank calculators 1908 and 1910 are input to a rank combiner 1912, which is operable to determine a rank based upon both rank predictions, one from the patient side and one from medical provider side based upon a patient query. For example, it might be that the patient preference results in a value of "9" on a scale of 0 to 10 for a typical medical provider but that medical provider shows a preference of "3" based upon the patient profile. It is important to keep in mind that this particular patient 1902 may never have interfaced with this particular medical provider but the model is basing the decision upon the general profile of the patient 1902 compared to other patients upon which the model 302 has been trained having a similar profile associated with the representation of the patient in the patient input vector. Since there are two different numbers, one algorithm employed by the rank combiner 1912 may be, in one disclosed embodiment, just to average the two values and come up with a value of "6." This is what would be presented to the patient 1902 in order for that patient to make a decision.

There is also provided an overall control block 1914 that can also receive inputs from the patient 1902 regarding the query provided thereby and this is operable to actually modify the way in which the rank combiner 1912 operates, i.e., the algorithm utilized thereby. This can also control the filtering operation for the medical provider data set 1906. An example would be location such that only available medical providers within a certain radius are selected from the medical provider data set 1906. Additionally, the control 1914 can receive control inputs that can be utilized to modify the overall prediction and ranking operation based upon certain system biases that may be introduced into this predictive system. In addition, the control block 1914 acting as a controller controls the overall operation of the model 302. When the patient 1902 enters the system, information regarding the patient and the query are entered into the system so as to allow creation of the two input vectors $x_{P-p}$ and $x_{P-mp}$ to the respective models 706 and 712. As discussed hereinabove, each of the models may use different vector values for the input. Certain vector values are important in the training of the different models 706 and 712, such that not all of the vector values provided by the patient 1902 (and from the data set 1904). The stored representation in the model 706 may be sensitive to one value representing the patient whereas the stored representation in the model 712 may not be sensitive to that one value. This is due to the fact that the model 706 on the patient side, during training, in determining a preference for a medical provider may consider some aspect representing a patient significant in the determination process. Conversely, the model 706 on the patient side, during training, in determining a preference for a patient may consider some aspect representing a patient significant in the determination process. When the patient information is input to the two models 706 and 712, this is a static input that remains the same for the ranking process.

The control block 1914 during operation of the model 302 is operable to sequence through the available medical providers in the available medical provider data set 1906 and provide the two input vectors $x_{MP-p}$ and $x_{MP-p}$ to the respective models 712 and 706. The vector values may be different for the same reasons described above for the patient inputs. During the sequencing, the control block 1914 will accrue information in the two rank blocks 1908 and 1910 and process them in the rank combiner 112. The output from the rank combiner is then forawarded to a display for viewing by the requesting patient. As noted, the information representing the requesting patient can be input on a keyboard or other input device or be extracted from the dat set 1904 or any combination thereof.

Figure 20:
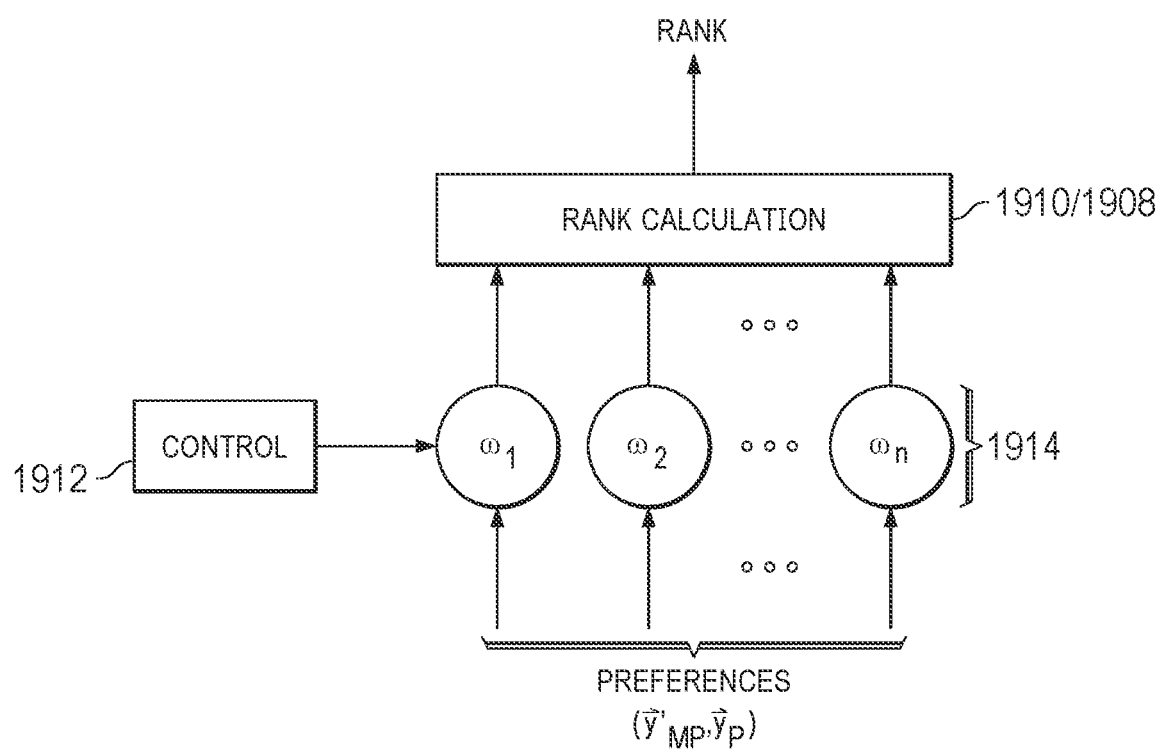
FIG. 20 illustrates a diagrammatic view of the rank conversion of the output vectors from the patient and medical provider models.

Referring to FIG. 20, there is illustrated a diagrammatic view of the one of the rank calculators 1908 or 1910 in an exemplary embodiment. As noted hereinabove, each of these rank calculators receives a plurality of preferences associated with the predicted preference output vectors $y_P$ or $y_{MP}$ which provides the medical provider preference predictions on the patient side or the patient preference predictions on the medical provider side of the model 302. In this embodiment, each of the predicted preference values $y_1$, $y_2$, $y_3$, . . . , $y_{n/m}$ are input to a weighting block 1914. Each of the preference values has associated therewith an individual weighting block 1914 labeled $\omega_1$, $\omega_2$, $\omega_3$, $\omega_{n/m}$. The control block 1912 controls these values from an external source. These weighting blocks 1914 each allow individual control of a particular preference. Consider the preferences set forth in the tabular view of FIG. 18 for the medical provider predicted preferences on the patient side and the model 706. Consider an additional preference not shown in this tabular view of, for example, "length of time" that a medical provider spent with a particular patient. In certain situations, a medical establishment might have a management objective of minimizing the amount of time that a medical provider interfaces with any particular patient. As such, it would be undesirable to provide any kind of weight to this particular preference as to ranking any medical provider; in fact, the system would rather rank a medical provider that spends less time on average with patients higher than one that spends a lot of time with the patient. Thus, initially all weighting factors are set to a value of "1," and they can be then changed to a lower value. If, for example, this preference of "length of time" were set to a value of "0.5," this would deemphasize that particular preference in the ranking. Thus, once a model is trained, it is possible to actually change the prediction output or proportionally weight that ouput against others. It should be understood that this rank calculation could be incorporated into the model. This variation of those weights is merely a way of modifying the prediction of a trained model, i.e., it actually modifies the prediction. Since a model is a function of variables that can be trained, such as weights and constants and the such, by allowing external access to these variables, the operation of the model can be changed, i.e., the stored representation of the preference predictions can be changed. Although only illustrated at the rank calculation level, this control can be implemented at any place in the model, depending upon how complex the model is. If it were just an algorithmic model of some sort, various constants could be changed.

Referring now to FIG. 21, there is illustrated a tabular view of one example of how the rank combiner 1912 operates based upon the asymmetric outputs of the patient and provider models. This illustrates the results for a new patient A' for predictions over nine medical providers. In the first two columns on the left, there is illustrated a first column 2102 listing the medical providers and a corresponding second column 2104 listing the rank determined by the medical provider model 706 and its associated rank calculator 1910 for patient A'. Illustrated in the third column and following in the top row are the medical providers with associated ranks based on the output of the patient model 706 and corresponding rank calculators 1908 for patient A'. For example, for medical provider "03," the patient preference prediction model 712 and rank calculator 1910 predicted a rank value of "7" in the column 2104. The medical provider preference model 706 and rank calculator 1908 for medical provider "03" predicted a rank value of "4" in the fifth column. An example of how this rank combiner might be configured to normalize values would be to add the two values together for a total of "11" and then divide that number by a factor of "2" to provide a rank value of "5.5" as an output from the rank combiner 1912. Compare this to the results for the medical provider "08" where the results from the model 712 and rank calculator 1910 yielded a rank value of "10" in column 2104 and where the model 706 and rank calculator 1908 yielded a rank value of "2" in the tenth column. This results in a total of "12" and a final value of "6." Thus, even though the patient preference model side ranked medical provider "03" twice as high as medical provider "08," medical provider "08" was actually ranked by the overall system model 302 twice as high. Again, this particular calculation is just one example of how the two rankings, each from a distinctly different and separately trained models, can be combined to provide a single predicted preference ranking. All of the values for all the medical providers could further be normalized.

Figure 22:
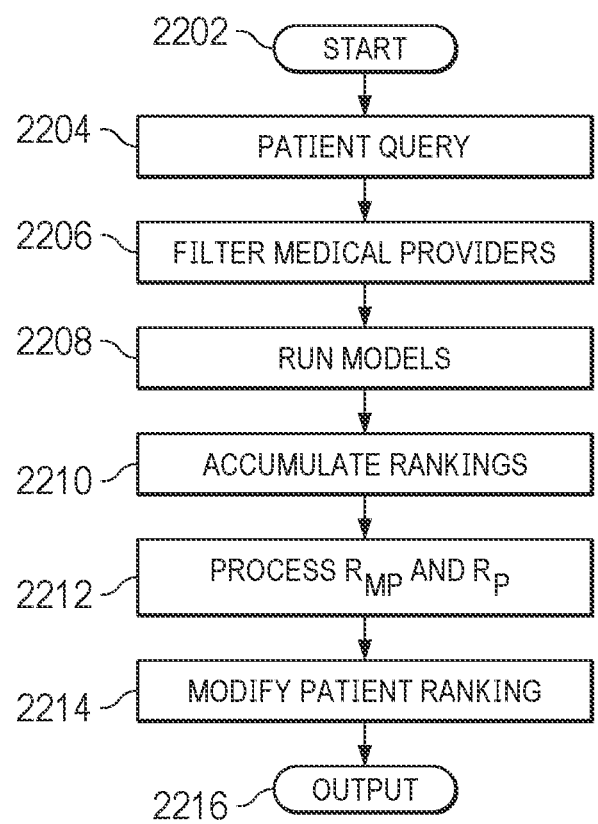
FIG. 22 illustrates a flow diagram of the operation of the ranking system.

Referring now to FIG. 22, there is illustrated a flow diagram of the operation of the ranking system to provide a rank list to a patient. The process is initiated at step 2202 and a patient query is entered at step 2204 for a list of potential medical providers. The initially provided list is filtered at step 2206 based upon details such as type of medical provider needed and geographic proximity to the patient. Next, at step 2208 the models generated as discussed hereinabove are run with respect to the patients and the potential or available providers. These rankings from the patients and the potential or available medical providers are accumulated at step 2210 based upon the output of the models. The provided medical provider rankings $R_{MP}$ and patient provider rankings $R_P$ are processed at step 2212. Processing involves receipt of the outputs of the patient ranking model and the medical provider ranking model that are each independently and separately trained. Information about the current patient is fed into both models as a digitally converted vector input representing the patient. The vectors may be different as required by the attributes or values associated with the vectors, but all information comes from the same current patient. The current patient information as a digitally converted vector representation of the current patient is provided into both models for each medical provider. This provides a patient preference prediction on the medical provider side and a medical provider preference on the patient side. FIG. 21 shows an example of one way a single ranking can be obtained from the two predictions in block 1912. The patient rankings may then be modified at step 2214 and at step 2216 as previously discussed with respect to FIG. 20 based on selected weighting values. As noted above, the patient desires a ranking of medical providers based on something for the purpose of making a decision as to what medical provider best suits their needs. The output of the medical preference model 706 with rank calculator 1908 will provide such a prediction, but only as to how a group of individuals with a similar digital vector representation to the requesting patient would have ranked a particular medical provider having a similar digital vector representation to each selected medical considered by the model 706. To this has been added a modification wherein patient preferences are predicted for each medical provider and this used to modify the patient side prediction of medical preferences of a data set of a requesting patient.

Figure 23:
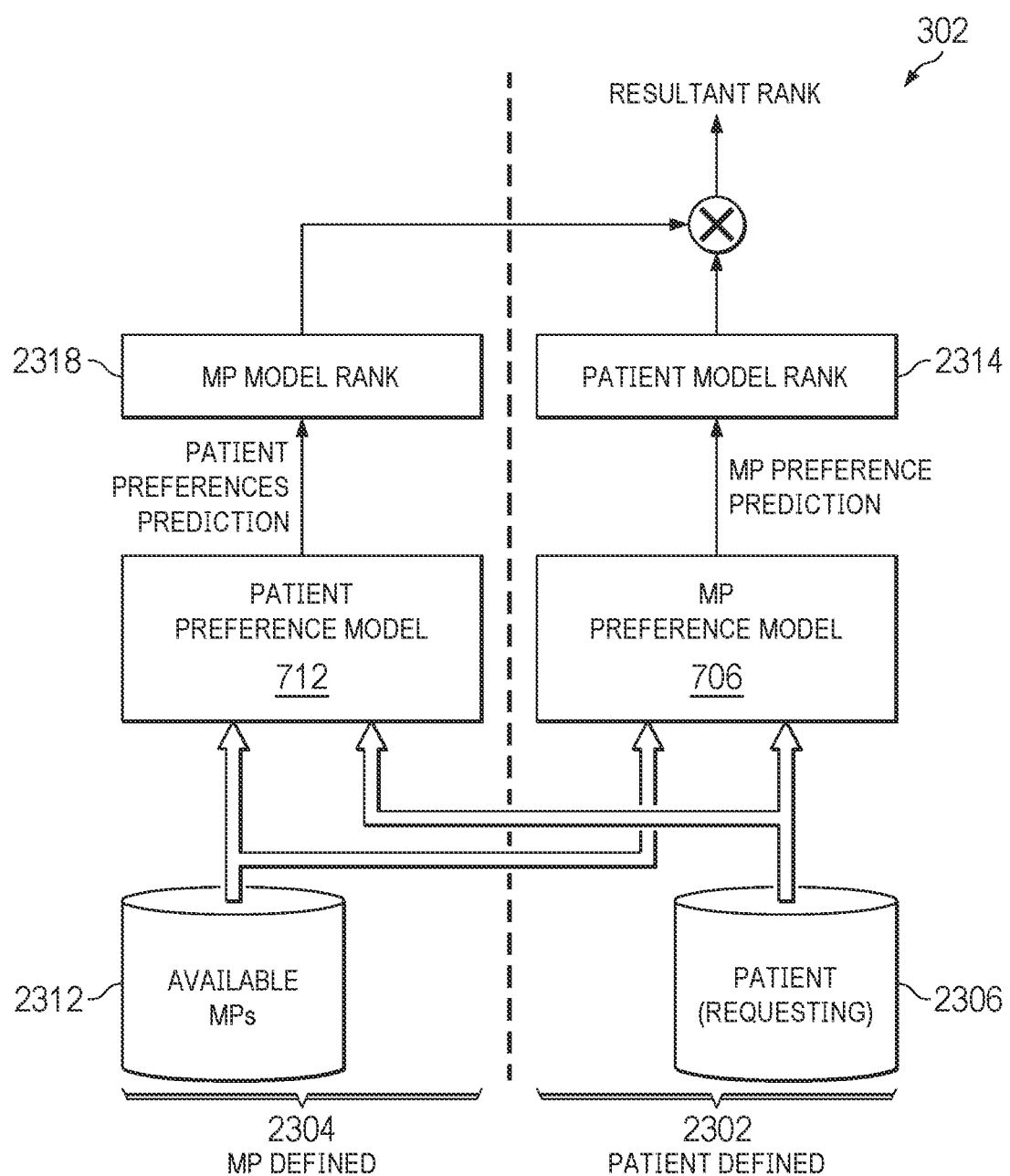
FIG. 23 illustrates a citified overall block diagram of the predictive ranking system in operation in response to a patient request for ranking of medical providers.

Referring now to FIG. 23, there is illustrated an overall block diagram of the operation of the model for receiving a patient request from a requesting patient and providing a ranking of the medical providers. In general, the overall model 302 is divided into a patient defined side 2302 and a medical provider defined side 2304. From a requesting patient's perspective, they would view any request for information regarding a medical provider to be something that is determined based on inputs from multiple patients. Thus, the model 706 would provide a preference model for medical providers based upon preferences of other patients similar to the requesting patient. Such a model is, as described hereinabove, trained on a patient side training data set that provides information from a plurality of patients regarding their preference for a particular medical provider they have ranked as to preferences. This patient side training data set is not a general data set of what a patient would like to see in a medical provider but, rather, this is a data set of feedback from patients on specific medical providers to whom they have been interfaced with respect to receiving medical services. Thus, each patient in the patient side training data set provides feedback on a particular medical provider, wherein each patient is defined by their attributes reflected in their patient input vector representation and each medical provider is defined by their attributes reflected in their medical provider input vector representation. Thus, the model 706, after training with the patient side training data set will provide a medical provider preference prediction on the output thereof.

In the illustration of FIG. 23, there is illustrated a new requesting patient 2306 that provides a request. From the perspective of the model 706, all that is required is that requesting patient 2306 be defined in terms of the attributes or values required to form the input vector to model 706, such that the requesting patient 2306 can be digitally converted into the patient input vector to the model 706. It could be that this information is contained in some medical data set, or this could be provided as new information. This basically defines the patient to the model in terms of a defined set of values that forms the patient input vector input to the model 706. Of course, although not shown, other information can be provided by the requesting patient 2306, such as location and such. This can be utilized to filter the overall operation. Any type of prediction would be better facilitated if only available medical providers were analyzed. As noted hereinabove, the model 706 requires as an input vector information regarding medical providers from a data set, such as a medical provider data set 2312. This medical provider data set 2312 can contain all medical providers in the system. It is important to note that it is not required for any of these medical providers to actually have been utilized for the training of the model 706; rather, all that is necessary is that each medical provider be realized with information that is required by the medical provider input vector to the model 706 for any given medical provider analyzed by the model 706, i.e., the information for a select medical provider is converted to a vector form compatible with the medical provider vector input to model 706. If the patient request can be limited to available medical providers, the ranking operation can be expedited. However, each medical provider input to the system in addition to the information regarding the patient will result in a prediction of a medical provider preference which can be utilized for ranking of medical providers.

If the requesting patient 2306 utilizes only the output of the model 706, preferences as to each of the processed medical providers would be provided. This can then be processed through a block 2314 in order to provide a ranking of the medical providers in the medical provider data set 2312. This alone would provide useful information to the requesting patient 2306, but this just provides information as to the preferences of a large number of patients similar to the requesting patient for medical providers.

By incorporating in the medical provider defined side 2304 of the model 302, this ranking on the patient defined side 2302 output from the block 2314 can be modified. As described hereinabove, the patient preference model 712 is defined by medical providers relative to patients that they have personally interfaced relative to medical services provided to those patients. The patient preference model 712 is trained using medical provider provided feedback with respect to the patients. Each medical provider with respect to a given patient provides feedback as to their preferences for this given patient. Each medical provider and each given patient, as was the case with respect to the training of a model 706, is defined by their particular attributes or values that form the respective medical provider and patient input vectors for the model 712. The preferences relative to that particular medical provider and the associated and given patient are associated with such. But again, as was the case with respect to the patient defined side 2302 and the description thereof, the operation of the model 712 based upon the attributes that comprise the medical provider input vector for the model 712 of each of the available medical providers in the data set 2312 and the attributes that comprise the patient input vector for the model 712 associated with the requesting patient 2306 may involve medical providers and a patient, i.e., the requesting patient, who have never interfaced with the system before. They are just defined in terms of the attributes associated therewith that comprise the input vectors for the model 712 form the input vectors to the patient preference model 712. As noted herein above, even though the medical provider data set 2312 and the patient 2306 contain information regarding, for a single process step for a selected medical provider, the patient input vectors and the medical provider input vectors can be different for each of the models 706 and 712. This is because they are separately trained models of two separate training data sets. There are certain attributes for a patient and a medical provider that only affect one of the models 706 or 712 in the training operation require to define a trained model.

When operated, this patient preference model will define a patient preference prediction on the output of the model 712, which provides a prediction based upon feedback information from a large group of medical providers regarding how those medical providers viewed patients they have interfaced with. This is an independent prediction that is not related to the prediction provided by the model 706. As noted herinabove, both the model 706 and the model 712 will typically be trained on the different medical providers and patients, although there could be an overlap when the training data sets were created, albeit small.

The patient preference prediction output by the model 712 is input to a medical provider model ranking block 2318 that is operable to provide a rank by a select one of the medical providers of the requesting patient based on their vector representation from the perspective of the vector representation of the select medical provider. The output of this block 2318 is utilized in conjunction with the output of the patient model ranking block 2314 in order to modify this patient model ranking value. Thus, the requesting patient that is requesting information does not just receive information regarding how other patients similar to them in general prefer each of the selected medical providers but, rather, modified information that takes into account how each of the medical providers preferentially ranks a patient having a similar vector representation to the requesting patient based on feedback from the medical providers. Just from the attributes associated with the vector representation of any given medical provider in the medical provider data set 2312, the model 712 and the model ranking block 2318 can determine how medical providers having a similar vector representation to the vector representation of the select medical provider would rank patients having a similar vector representation to the vector representation of the requesting patient 2306. Without this modification utilizing the medical provider defined side 2304 of the model 302, it is possible that the model 706 and the ranking block 2314 could rank a given medical provider relatively high, wherein the given medical provider actually has no interest in interfacing with this requesting patient 2306.

It can be seen from the block diagram in FIG. 23 that the model is operated based upon a new patient 2306 desiring information about a group of medical providers, wherein such information is ranked to provide this new patient 2306 with a list of suggested medical providers. It is possible that this model 302 could be operated in the reverse order. If a medical provider, for some reason, wanted information regarding a particular patient, all that would be required is for the patient, for example, the patient 2306, to input their information into the model 302 which would generate a single preference prediction on the model 712 on the medical provider defined side 2304 as to how a model of preferences of medical providers for patients in general would predict how this particular medical provider would rank this particular patient 2306 as to whether they would prefer them or not. The patient defined side 2302 would then predict how a model of preferences of patients for medical providers in general would protect how this particular patient 2306 would rank them. The question would be—why would a single medical provider have any interest in knowing how a medical provider similar to them would be predicted as to preferences for this particular patient in addition to how this given patient might be predicted as to their preference for them. Of course, an individual medical provider really has no interest in any kind of ranking system to provide a list of patients, unless they are seeking new patients from a data set of available patients for some reason.

The "confidence" level of a model is a function of the architecture of the model, but more importantly, the quality of the training data. Any training data has a defined data "space" that defines how much data is taken in a particular data area of relevance. For example, in a training data that might be utilized to train the models 706 and 712, relevant data would be medical providers and patients that are in an area proximate to where the requesting patient 2306 lived. If the requesting patient 2306 were from New York, for example, a training data set of New York residents that lived proximate to the area inhabited by the requesting patient 2306 would provide fairly relevant data to any prediction. However, if a visitor from Africa were to enter the request into the model 302 for medical providers in the New York area, the confidence level of the prediction would be relatively low. And this would be even more so if it were for a malady that was more prevalent in Africa. This confidence level is in part based upon the density of relevant data in the data space related to the request and upon which the models were trained. This request, of course, is defined based upon the input vector from the patient. As new requesting patients enter the system, more data is collected into available data sets regarding preferences. Retraining of the models 706 and 712 can be automatically scheduled on a periodic basis, the understanding that the collection of data yields additional data or more timely and relevant data. Additionally, a threshold situation can be determined wherein a sparsely populated portion of the data space in the training data set has, for some reason, become associated with a plurality of new requests. An example could be related to the type of malady associated with the request. If the requesting patient 2306, for example, were requesting information regarding a list of medical providers for a simple thing such as knee pain, there is a high likelihood that the training data utilized in training models 706 and 712 are well populated with that type of request and associated preference information. However, if all of a sudden, a new virus came upon the scene, information regarding a ranking list for medical providers that would specialize in treating this new virus would be minimal. The model would actually predict a ranking order of medical providers that had some experience with viral infections, such as infectious disease experts, but the experience with this particular new virus could be minimal at first. The confidence level of this prediction is thus relatively low. This is a result of the training data being sparsely populated for medical providers with a high level of experience with this new virus. As the virus spreads through the population in a particular area, more and more medical providers will be available at this higher level of experience. Without retraining the models 706 and 712, the rank provided to the requesting patient has a much lower confidence level than the situation where in the models 706 and 712 were trained with new data including the more experienced medical providers.

In the overall operation of the trained model 302, the requesting patient is provided with information regarding a plurality of medical providers in order to make an informed decision regarding a particular medical query. Without the model 302, it would be difficult for a requesting patient to make use of the experience of a large number of patients making a similar query. For example, consider the patient side of the model without the medical provider side of the model. If a patient or, for example, a runner having a sprained knee, that runner might want to seek some medical intervention in the form of selecting the best physician to address this sprained knee. In a normal query that a human would make, they might ask another runner who they would select. They may even query a number of different runners they know who had a similar situation with a sprained knee and had sought medical intervention. If this were the case, they were merely asking for a recommendation for a physician. The model 706, on the other hand, starts out with not just the query but also with a list of physicians upon which to obtain a recommendation. Suppose that this runner had a medical plan that only had three physicians listed as available under the plan. This runner then might ask one or two runners that they knew who had sprained knees if they had actually had their sprained knee worked on by any of these particular physicians on the plan. The model 706 on the patient side allows the query by the runner to be analyzed in terms of how a plurality of patients looking for substantially the same information and who were very similar to runner how they had viewed the physician at the time of their interface with that physician. The requesting patient or runner is not only looking for just a person seeking the same information but, rather, a person that was seeking the same information regarding a similar medical condition, had found the solution to that query in the form of selecting a physician to address that medical condition and how that interface with the physician was viewed by that particular person. The model 706 alone provides very relevant information for just a single request for information regarding a single physician to treat a specific malady because it is based on at least one other patient that is "similar" to the requesting patient having interfaced with that single physician and having provided some feedback as to their experience with that single physician. This is not something that an individual would do when making an informed decision, as trying to determine how one would themselves make a decision is not important; rather, all that is important is to query other individuals for feedback of any sort on a particular physician. Some patients might ask a physician in another specialty who they would recommend for the particular malady. However, this particular recommending physician only makes a decision as to how they would make a decision, i.e., "If I were you, I would choose this position." This recommending physician may just be someone that the requesting patient respects but they are not seeking their advice because that particular recommending physician is similar to them, nor are they presenting a group of potential physicians to the recommending physician in that decision-making process. The model 706 allows a requesting patient to ask the question-"How would I rank this physician if I allowed them to treat my particular malady"? That is not the query that the particular human would make in trying to make an informed decision. They just collect a lot of information and then they make the decision based upon that information. And, when this is applied to a group of available or potential physicians come this easy more so something that a human would not do or employ in their decision-making process.

When the medical provider side of model 302 is implemented, this is a distinctly different process than any human would ever employ in any decision-making process. Further, when implementing two models that are each independently and separately trained on two independent and separate training data sets, this provides to distinct queries, i.e., the requesting patient wants to know "How would I rank this physician if I allowed them to treat my particular malady" and "How would this physician ranked me as a patient"? When combining both sides of the model 302, the patient model 706 and the medical provider model 712, a patient is provided with the ability to select from a list of available medical providers the best fit for them because they are able to determine how other patients similar to them would rank each of these medical providers and, further, the overall model 302 would provide this information based upon a predicted input from each of the medical providers in the form of a predicted ranking for that particular patient which can be utilized to modify any ranking list.

In the operational mode, the embodiment of FIG. 23 utilizes the data set 2312 to provide information regarding available medical providers and data set 2306 that is generated when a requesting patient enters the system. In this mode, the model 302 comprised of both the medical provider preference model 706 on the patient side and the patient preference model 712 on the medical provider side both comprise fixed models, i.e., the variable weights or constants associated with the type of model implemented are "fixed." In this operation, as described hereinabove, the inputs to both of the models 706 and 712 receive information from the same data set 2312 and the same patient.

In certain situations, the operation of the model 302 can be determined to require additional learning, i.e., there is a possibility that the confidence level in the ranking is less than optimum. For example, it may be noticed that the patients are continually selecting less than the top one or two selections. If in requesting information about an orthopedic surgeon, by way of example, it is notice that the patients are always requesting a certain orthopedic surgeon on the list that is not ranked as high as others, an adjustment to the overall model 302 might be warranted. It is noted that, after the ranking is presented to the requesting patient, the patient will actually select one of the ranked available medical providers that are present in the data set 2312. This adjustment is basically a retraining or relearning of the overall model 302. Since, as described hereinabove, each of the models 706 and 712 are discrete models trained on different databases, it might be necessary to retrain one or both of the models 706 and/or 712. In this retraining mode, one technique may be to utilize updated data in the training data sets 1102/1102' and 1104/1104' for the respective models 712 and 706. This requires detaching the model in the operational mode from the data sets 2312 and 2306.

It is possible that one of the values of the vector that represents any given medical professional could be an indication of selected/unselected/null meaning that in some previous ranking operation, that particular medical provider was selected. Since a medical provider is defined in the system as a vector representation, repeated selection of one or more medical providers with a similar vector representation could result in the system changing the value to either selected or unselected, depending upon the results in the operational mode of the model 302. This would be a change that would be made to at least the data set 1102 associated with the training of the model 712 and one example, and possibly to the data set 1102' for the training of the model 706. For the model or models that are to be retrained, they are detached from the data set 2312 and the data set 2306 and retrained.

In another retraining operation, it may be that surveys taken after the interface of a requesting patients with a selected available medical providers based upon their ranking by the model 302 exhibits somewhat unsatisfactory results, is it possible that retraining is justified. In some situations, updated training data sets 1102/1102' and 1104/1104' can be utilized. These data sets 1102/1102' and 1104/1104' are data sets that are created from patients utilizing the model 302, for example. They can also be created just from patients interfacing with different medical providers and providing preferences therefore. Overall, these training data sets are generated based upon different entities taking surveys, for example, from patients regarding medical providers. With information regarding medical providers, the patients and at the least preferences of the patients for the medical providers, new data sets 1102' and 1104' can be created. If the number of data sets are large enough, it might be possible to retrain the model 706 and the model 712 with data from a different region in a situation where, for example, the demographics of the particular region or hospital area had changed. This also may be the case when a new viral pandemic occurs which could change the preferences of patients for any particular medical provider. It also may be that the only model has to be retrained is the medical provider preference model 706 on the patient side. However, retraining of both models can be done in response to some change or indication of a low confidence level in the model or just periodically based upon age of the original training data sets 1102/1102' and 1104/1104'.

The result of the retraining is to again provide two separate and discrete models 706 and 712, each trained on a separate and independent training data set. The representation stored in each of the models 706 and 712 contains a different representation. The representation stored in model 706 is a representation of the preferences of patients for a medical provider and the representation stored in the model 712 is a representation of the preferences of medical providers for a patient. As such, a patient seeking information on a medical provider would see in the model 706 alone what other patients "similar" to the requesting patient would think of an available medical provider "similar" to an available medical provider. These other patients in the training data set have never met this requesting patient nor have they ever met or interfaced with the available medical provider that is being ranked. If just the model 706 were used, all that a patient would receive would be the input of other patients. With the addition of the model 712, an additional level of input is provided regarding the medical provider's preference for this patient, albeit relating to a similar patient representation of this patient. But the actual available medical provider does not really care about this aspect and would see the patient anyway. The available medical provider may not even be aware that they are being ranked lower or higher by the model 302. The available medical provider is not involved in the ranking operation other than that they are in the available medical provider data set 1906. All the requesting patient is looking for is the recommendation of other patients and the model 302 utilizes the medical provider side model 712 to improve the ranking, such that is an asymmetrical decision process. It should be understood that, although the model 302 is described relative to patients and medical providers, it can be used for other situations where preferences are relevant.

It will be appreciated by those skilled in the art having the benefit of this disclosure that this machine learning system for asymmetrical matching of care givers and care receivers provides an improved manner for generating a ranked list of medical providers for considerations by a patient. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for selection of a medical provider (MP) by a requesting patient based on preferences for the MP, comprising:
    a first primary model for modeling preferences of a plurality of patients for select MPs and trained on a first training data set comprised of patients and MPs, wherein the patients in the first training data set have rated at least one of the MPs in the first training data set by a predetermined set of patient determined preferences, the first primary model having a first model patient input for receiving information representative of the requesting patient, a first model MP input for receiving information representative of an available MP and a MP preference output for outputting a patient determined preference of the requesting patient for an available MP based on a learned representation of the patient determined preferences in the first training data set in response to a query from the requesting patient;
    a second modifying model for modeling preferences of a plurality of MPs for select patients and trained on a second training data set comprised of MPs and patients, wherein the MPs in the second training data set have rated at least one of the patients in the second training data set by a predetermined set of MP determined preferences, the second modifying model having a second model patient input for receiving information representative of the requesting patient, a second model MP input for receiving information representative of an available MP and an MP determined preference output for outputting an MP determined preference of an available MP for the requesting patient based on a learned representation of the MP determined preferences in the second training data set in response to the query to the first primary model from the requesting patient;
    an available MP data set containing information representative of available MPs for selection thereof by the requesting patient;
    a controller for controlling the first primary model and second modifying model to select at least a portion of the available MPs in the available MP data set for input of the associated information representative of the at least a portion of the available MPs to the first primary model and the second modifying model MP inputs of the first primary model and the second modifying model;
    the controller controlling the first primary model and the second modifying model to sequence through the selected at least a portion of the available MPs;
    a patient rank calculator to accumulate the output patient determined preferences for MPs associated with the selected at least a portion of the available MPs and generate a MP ranking for each of the selected at least a portion of the available MPs;
    a MP rank calculator to accumulate the output MP determined preferences for the requesting patient for each of the selected at least a portion of the available MPs and generate a patient ranking for each of the selected at least a portion of the available MPs; and
    a modifier for modifying the patient ranking output of the patient rank calculator with the output of the MP rank calculator to provide as an output in response to the query from the requesting patient a resultant ranking list for each of the selected at least a portion of the available MPs.

2. The system of claim 1, wherein the MPs in the first and the second training data set and the patients in the first and the second training data set are different.

3. The system of claim 1, wherein at least one of the MPs in the first and the second training data sets are the same.

4. The system of claim 1, wherein at least one of the patients in the first and the second training data sets are the same.

5. The system of claim 1, wherein the patient determined preferences associated with the first primary model comprise a rank value.

6. The system of claim 1, wherein the patient determined preferences associated with the first primary model comprise a plurality of different values representative of different types of preferences of a patient for a medical provider.

7. The system of claim 6, wherein the patient determined preference includes at least a portion of the plurality of different values as output values.

8. The system of claim 7, and further comprising weighting blocks for at least a portion of the at least a portion of the output values in the patient determined preference, wherein each of the weighting blocks has a variable weight associated with one of the output values, and controlled by the controller to vary a value of the associated one of the output values.

9. The system of claim 1, wherein the MP determined preferences associated with the second modifying model comprise a plurality of different values representative of different types of preferences of an MP for a patient.

10. The system of claim 9, wherein the patient determined preference includes at least a portion of the plurality of different values as output values.

11. The system of claim 1, wherein the information representative of the available MPs in the available MP data set is comprised of a plurality of MP values that uniquely identify each of the MPs contained therein.

12. The system of claim 11, wherein the first model MP input is associated with a first subset of the plurality of MP values and the second model MP input is associated with a second subset of the plurality of MP values.

13. The system of claim 12, wherein a portion of the first subset overlaps with the second subset.

14. The system of claim 12, wherein the first and second subset are identical.

15. The system of claim 12 wherein the MPs in the first training data set for the first primary model are represented by at least a portion of the plurality of MP values in the first subset and the MPs in the second training data set for the second modifying model are represented by at least a portion of the plurality of MP values in the second subset.

16. The system of claim 1, wherein the information representative of the requesting patient is comprised of a plurality of patient values that uniquely identify the requesting patient.

17. The system of claim 16, wherein the first model patient input is associated with a first subset of the plurality of patient values and the second model patient input is associated with a second subset of the plurality of patient values.

18. The system of claim 17 wherein the patients in the first training data set for the first primary model are represented by at least a portion of the plurality of patient values in the first subset and the patients in the second training data set for the second modifying model are represented by at least a portion of a plurality of MP values in the second subset.

19. The system of claim 17, wherein a portion of the first subset overlaps with the second subset.

20. The system of claim 17, wherein the first and second subset are identical.

\* \* \* \* \*

UNITED STATES PATENT AND TRADEMARK OFFICE
CERTIFICATE OF CORRECTION

PATENT NO. : 11,791,038 B1
APPLICATION NO. : 17/979602
DATED : October 17, 2023
INVENTOR(S) : Michael Sheehan et al.

It is certified that error appears in the above-identified patent and that said Letters Patent is hereby corrected as shown below:

On the Title Page

Item (12) should read:
Sheehan et al.

Item (72) should read:
(72) Inventors: Michael Sheehan, Flower Mound, TX (US);
Stephen Brobst, Las Vegas, NV (US);
John Trustman, Frisco, TX (US);
Michael McDonald, Dallas TX (US)

Signed and Sealed this
Twentieth Day of August, 2024

Katherine Kelly Vidal
*Director of the United States Patent and Trademark Office*